(12) United States Patent
Troy et al.

(10) Patent No.: US 10,162,352 B2
(45) Date of Patent: Dec. 25, 2018

(54) REMOTELY OPERATED MOBILE STAND-OFF MEASUREMENT AND INSPECTION SYSTEM

(71) Applicant: The Boeing Company, Chicago, IL (US)

(72) Inventors: James J. Troy, Issaquah, WA (US); Scott W. Lea, Renton, WA (US); Gary E. Georgeson, Tacoma, WA (US); William P. Motzer, Mount Pleasant, SC (US)

(73) Assignee: The Boeing Company, Chicago, IL (US)

( * ) Notice: Subject to any disclaimer, the term of this patent is extended or adjusted under 35 U.S.C. 154(b) by 0 days.

(21) Appl. No.: 15/796,880

(22) Filed: Oct. 30, 2017

(65) Prior Publication Data

US 2018/0067484 A1 Mar. 8, 2018

Related U.S. Application Data

(63) Continuation-in-part of application No. 13/892,336, filed on May 13, 2013, now Pat. No. 9,804,577.

(51) Int. Cl.
| | | |
|---|---|---|
| *G05D 1/00* | (2006.01) | |
| *G01S 17/08* | (2006.01) | |
| *G01S 17/88* | (2006.01) | |
| *G01N 29/04* | (2006.01) | |
| *G01N 29/06* | (2006.01) | |
| *G01N 29/44* | (2006.01) | |
| *G05B 15/02* | (2006.01) | |
| *H04N 7/18* | (2006.01) | |

(Continued)

(52) U.S. Cl.
CPC ......... *G05D 1/0033* (2013.01); *G01N 29/043* (2013.01); *G01N 29/0654* (2013.01); *G01N 29/4472* (2013.01); *G01S 17/08* (2013.01); *G01S 17/88* (2013.01); *G05B 15/02* (2013.01); *G05D 1/0022* (2013.01); *H04N 7/185* (2013.01); *G01S 17/023* (2013.01); *G01S 17/06* (2013.01)

(58) Field of Classification Search
None
See application file for complete search history.

(56) References Cited

U.S. PATENT DOCUMENTS

| | | |
|---|---|---|
| 3,550,547 A | 12/1970 | Pleuger |
| 4,625,938 A | 12/1986 | Brown |
| | (Continued) | |

FOREIGN PATENT DOCUMENTS

WO 2008134762 A1 11/2008

*Primary Examiner* — Frederick D Bailey
(74) *Attorney, Agent, or Firm* — Ostrager Chong Flaherty & Broitman P.C.

(57) ABSTRACT

Self-contained, remotely operated, mobile measurement and inspection systems for stand-off inspection of large target objects located at sites distant from an operations center. The systems comprise a mobile platform with on-board instrumentation capable of making dimensional measurements in the local coordinate system of the target object. The systems comprise multiple hardware and software components networked to a control interface that enables the operator at the operations center to teleoperate the equipment. Various embodiments include rough-terrain and floatable mobile measurement and inspection systems.

22 Claims, 18 Drawing Sheets

(51) Int. Cl.
*G01S 17/02* (2006.01)
*G01S 17/06* (2006.01)

(56) References Cited

U.S. PATENT DOCUMENTS

| | | | |
|---|---|---|---|
| 4,710,819 A | 12/1987 | Brown | |
| 5,113,768 A | 5/1992 | Brown | |
| 5,528,453 A * | 6/1996 | Berman | A45C 5/14 280/47.26 |
| 5,627,616 A | 5/1997 | Sergeant et al. | |
| 5,924,069 A * | 7/1999 | Kowalkowski | G10L 15/26 704/270 |
| 6,658,325 B2 | 12/2003 | Zweig | |
| 6,798,343 B2 * | 9/2004 | Carrier | A62C 27/00 340/539.13 |
| 7,013,939 B2 | 3/2006 | Rhyne et al. | |
| 7,088,071 B2 | 8/2006 | Rodnunsky | |
| 7,859,655 B2 | 12/2010 | Troy et al. | |
| 8,044,991 B2 | 10/2011 | Lea et al. | |
| 8,223,208 B2 | 7/2012 | Alexander | |
| 8,255,170 B2 | 8/2012 | Kollgaard et al. | |
| 8,447,805 B2 | 5/2013 | Troy et al. | |
| 8,744,133 B1 | 6/2014 | Troy et al. | |
| 9,285,296 B2 | 3/2016 | Georgeson et al. | |
| 9,433,849 B1 | 9/2016 | Brown | |
| 2002/0096844 A1 | 7/2002 | Clegg | |
| 2004/0001750 A1 | 1/2004 | Kremerman | |
| 2006/0228201 A1 * | 10/2006 | Lenceski | A63B 71/0036 414/466 |
| 2007/0076096 A1 * | 4/2007 | Alexander | H04N 5/2226 348/169 |
| 2007/0206115 A1 | 9/2007 | Kuo | |
| 2008/0307886 A1 | 12/2008 | Marsh et al. | |
| 2009/0086199 A1 | 4/2009 | Troy et al. | |
| 2012/0221625 A1 | 8/2012 | Troy et al. | |
| 2012/0316913 A1 * | 12/2012 | Reyes | G06Q 50/08 705/7.23 |
| 2013/0298816 A1 | 11/2013 | Van Der Kam | |

\* cited by examiner

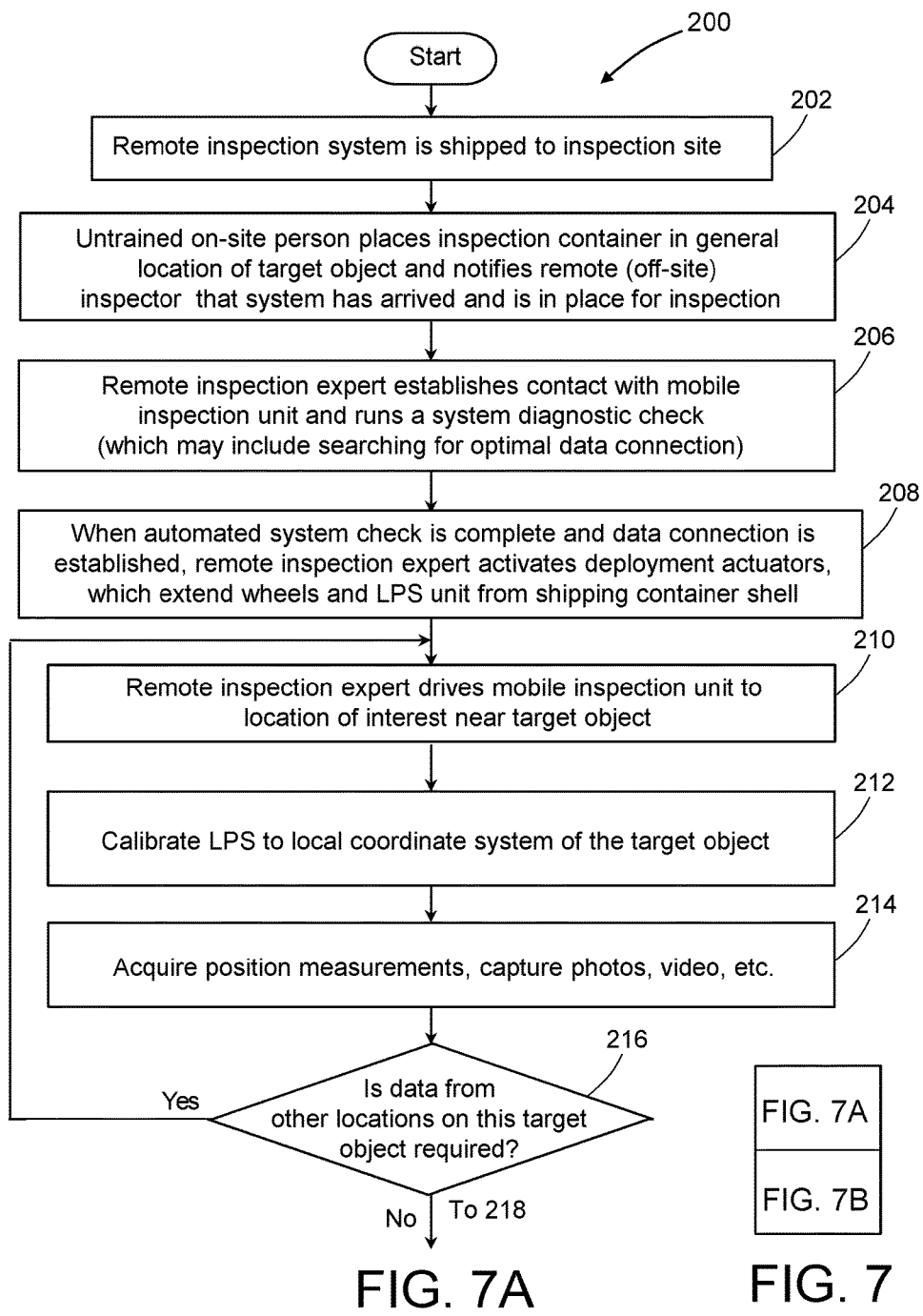

REMOTELY OPERATED MOBILE STAND-OFF MEASUREMENT AND INSPECTION SYSTEM

RELATED PATENT APPLICATIONS

This application is a continuation-in-part of and claims priority from U.S. patent application Ser. No. 13/892,336 filed on May 13, 2013 (issued as U.S. Pat. No. 9,804,577 on Oct. 31, 2017), which application in turn is a continuation-in-part of and claims priority from U.S. patent application Ser. No. 13/166,613 filed on Jun. 22, 2011 (issued as U.S. Pat. No. 9,182,487 on Nov. 10, 2015) and U.S. patent application Ser. No. 12/897,408 filed on Oct. 4, 2010 (issued as U.S. Pat. No. 8,744,133 on Jun. 3, 2014). The disclosures of the three patent applications identified in this paragraph are hereby incorporated by reference herein in their entireties.

BACKGROUND

The disclosure relates to position measurement for repair and maintenance management of structures. More particularly, the disclosure relates to systems and methods for non-contact non-destructive measurement and inspection of structures.

When repair work is required on a structure, it may be necessary to take into account the size, shape and location of previous damage and/or repairs for optimum repair of the structure. Photographs of the previous damage and/or repair may be made but may not be precisely located or sized on the structure or may not be useful for future repair planning. During the analysis of a damage/repair site (i.e., a location of interest), it may be desirable to obtain measurement information without contacting the target object. Due to accessibility and/or contact constraints, it may be difficult to reach the location of interest to obtain position measurements. Therefore it is advantageous for a local positioning system to be able to take measurements without contacting the target object and from moderate to large distances from the target object. Local positioning systems capable of stand-off measurement of a target object may utilize acoustic, laser-based, magnetic, RFID, GPS, and motion capture-based systems.

Finding and accurately measuring the locations of potential damage on a structure such as a storage tank or on a large vehicle such as a commercial airplane can be a laborious task. An efficient and automated process for addressing this problem would be valuable to many organizations involved in building and maintaining large vehicles and structures.

Prior inspection processes required inspection experts to be present with the measurement hardware at the site of the airplane (or other target object) being inspected. In accordance with that process, the inspection expert is required to travel to the inspection site, set up the equipment, and then perform the inspection. The end-to-end time requirement could be several days, depending on how far the expert had to travel.

Other semi-automated systems allowed remote operation of stationary measurement hardware, but still required an on-site assistant in order to set up and move the measurement instruments into position. One stand-off inspection system combines a local positioning system (LPS) with a nondestructive inspection (NDI) method to replace inspector's manual labor, increase the inspection rate, and find much smaller cracks than what can be seen visually, without physically touching the large target object. Another inspection system combines a stand-off local positioning system positioned adjacent to a large target object (i.e., at the inspection site) with an NDI scanner mounted to the target object. In accordance with the teachings of U.S. Pat. No. 9,182,487, the system can be configured and programmed with remotely operated hardware and software components to enable data collection by an expert NDI analyst from an off-site operations center, with the only on-site assistance coming from non-expert support personnel to setup the local positioning system and NDI scanning hardware.

Furthermore, an NDI scanner mounted to a target object may be more difficult to use due to the contact between the sensor and the surface being inspected. For example, in-service NDI scans can be challenging because there any many structural elements (e.g., lightning protection, stiffeners, ramped back surfaces, etc.) that can add to the scan complexity. This can lead to extended inspection times, mistakes, or further inspections in order to increase the clarity of the results.

It would be advantageous if a remotely operable mobile system for NDI of a large target object, such as a storage tank or an airplane, could be set up at the inspection site with minimal on-site personnel assistance. In addition, it would be advantageous to employ a system for measurement and inspection which did not require contact with the target object. Accordingly, a mobile telepresence system capable of performing stand-off measurement and/or inspection of a large target object would be advantageous.

SUMMARY

Self-contained, remotely operated, mobile standoff measurement and inspection systems for stand-off inspection of large target objects located at sites distant from an operations center of a distributed inspection system are disclosed herein. The systems comprise a mobile platform with on-board instrumentation capable of making dimensional measurements in the local coordinate system of the target object. More specifically, the systems comprise multiple hardware and software components networked to a control interface that enables the operator at the operations center to teleoperate the equipment, including driving or piloting the mobile platform to a location near an area of interest on a surface of the target object, calibrating the on-board local positioning system, acquiring measurement and image data, and communicating with on-site personnel if needed.

The ability to operate all of the hardware and software components remotely enables data collection by an expert analyst from an off-site operations center, with minimal on-site assistance. In accordance with various embodiments disclosed in some detail below, the system is transformable from an integrated enclosure for shipping, to a mobile configuration for self-propelled movement to the inspection location, and then to a measurement acquisition configuration. Various embodiments include even-terrain, uneven-terrain and floatable mobile measurement and inspection systems.

The ability of the inspection equipment to be self-contained and reconfigured remotely allows the remote operator of the system to be self-sufficient. It is not necessary to have a qualified person set up the measurement system at the inspection site. Additional system telepresence capabilities (such as two-way audio and video, plus the ability to point out locations) allow remote users of the system to interact with others at the inspection site if necessary.

One aspect of the subject matter disclosed in detail hereinafter is a mobile system comprising: a shipping container; a multiplicity of compliant non-pneumatic tires mechanically coupled to the shipping container for movement between respective retracted positions in a shipping configuration and respective extended positions in a deployed configuration; a local positioning system unit mechanically coupled to the shipping container for movement between a retracted position inside the shipping container in the shipping configuration and an extended position outside the shipping container in a deployed configuration, the local positioning system unit comprising a laser range meter and a video camera; a computer system disposed inside the shipping container; a transceiver communicatively coupled to the computer system and capable of receiving commands from an in-range wireless network access point and transmitting the commands to the computer system; a drivetrain disposed inside the shipping container for driving at least one of the compliant non-pneumatic tires to rotate; a wheel deployment actuator disposed inside the shipping container for actuating movement of a first compliant non-pneumatic tire of the multiplicity of compliant non-pneumatic tires between its retracted and extended positions; and a local positioning system unit deployment actuator disposed inside the shipping container for actuating movement of the local positioning system unit between its retracted and extended positions. The computer system is configured to perform the following operations: controlling the wheel and local positioning system unit deployment actuators in response to deployment commands received via the transceiver; controlling the drivetrain to move the shipping container to a location near a target object in accordance with a platform location command received via the transceiver when the compliant non-pneumatic tires are in their extended positions; and controlling the laser range meter to project wave energy toward a point on a surface of the target object.

Various embodiments of the system described in the preceding paragraph include one or more of the following features:

(a) The computer system is further configured to control the local positioning system unit to calibrate its position and orientation relative to a coordinate system of the target object in response to a calibration command received via the transceiver.

(b) The mobile system further comprises a lift mechanism pivotably coupled to the shipping container, coupled to the local positioning system unit deployment actuator, and having stops at fully extended and fully retracted positions, wherein the local positioning system unit is mounted to the lift mechanism.

(c) The video camera has a focal axis, the laser range meter has an axis parallel to the focal axis of the video camera, and the video camera is mounted to a motorized pan-tilt mechanism.

(d) Each of the multiplicity of compliant non-pneumatic tires (a.k.a. compliant airless tires) comprises a respective outer band made of elastomeric material.

(e) The mobile system further comprises an inertial measurement unit mounted inside the shipping container, wherein the computer system is configured to estimate a location of the mobile system based at least in part on signals received from the inertial measurement unit.

(f) Optionally, the shipping container can be equipped with an antenna and a GPS receiver, which receive geolocation and time information in a well-known manner. The GPS receiver may communicate with the computer system, which may include a processor configured to calculate the geolocation of the shipping container. The same processor can be further configured to check the system for correct right-side-up orientation for safe deployment (using orientation data acquired by the inertial measurement unit) and correct position to make sure that the mobile system is at a correct site (using geolocation data acquired by the GPS receiver).

Another aspect of the subject matter disclosed herein is a method for teleoperation of a mobile system from a remote computer, comprising: (a) configuring the mobile system comprising a shipping container so that a multiplicity of compliant non-pneumatic tires are in retracted positions and a local positioning system comprising a video camera and a laser range meter is in a retracted position in a shipping configuration; (b) placing the mobile system in the shipping configuration on an uneven surface at a site; (c) establishing a communication channel between a computer system inside the shipping container and the remote computer via a wireless connection while the mobile system is at the site; and (d) via the wireless connection, remotely activating a transformation of the mobile system from the shipping configuration to a deployed configuration in which the compliant non-pneumatic tires and the local positioning system are in respective extended positions.

In accordance with one embodiment, the method described in the preceding paragraph further comprises: via the wireless connection, remotely controlling rotation of at least one compliant non-pneumatic tire to cause the mobile system in the deployed configuration to travel over the uneven surface to a location in proximity to a target object; acquiring linear acceleration and rotational rate data using an inertial measurement system that is fixed relative to the shipping container as the mobile system travels over the uneven surface; using the linear acceleration and rotational rate data from the inertial measurement system, differential odometry tracking, and a dead reckoning algorithm to compute an estimate of the position and orientation (location) of the shipping container; remotely activating the laser range meter to measure a distance to a point on a surface of the target object; and remotely activating the video camera to capture an image of an area on the surface of the target object.

A further aspect of the subject matter disclosed in detail hereinafter is a mobile system comprising: a shipping container; a multiplicity of ducted propeller units mechanically coupled to the shipping container for movement between respective retracted positions in a shipping configuration and respective extended positions in a deployed configuration; a local positioning system unit mechanically coupled to the shipping container for movement between a retracted position inside the shipping container in the shipping configuration and an extended position outside the shipping container in the deployed configuration, the local positioning system unit comprising a laser range meter and a video camera; a computer system disposed inside the shipping container; a transceiver communicatively coupled to the computer system and capable of receiving commands from an in-range wireless network access point and transmitting the commands to the computer system; a propeller deployment actuator disposed inside the shipping container for actuating movement of a first ducted propeller unit of the multiplicity of ducted propeller units between its retracted and extended positions; and a local positioning system unit deployment actuator disposed inside the shipping container for actuating movement of the local positioning system unit between its retracted and extended positions. The computer system is configured to perform the following operations: controlling the propeller and local positioning system unit deployment actuators in response to deployment commands received via the transceiver; controlling the ducted propeller units to move the shipping container to a location near a target object in accordance with a platform location command received via the transceiver when the ducted propeller units are in their extended positions; and controlling the laser range meter to project wave energy toward a point on a surface of the target object.

Various embodiments of the floatable system described in the preceding paragraph include one or more of features (a) through (c), (e) and (f) described above. In addition, each of the multiplicity of ducted propeller units comprises a propeller, a nozzle (or shroud) that surrounds the propeller, a propeller thrust motor supported by the nozzle and having an output shaft coupled to the propeller for driving it to rotate to generate thrust, and a propeller yaw control motor that drives rotation of the ducted propeller unit about a yaw axis. The computer system is further configured to control to propeller thrust motors and the propeller yaw control motors to provide independent thrust and yaw control for each ducted propeller unit.

Yet another aspect is a method for teleoperation of a mobile system from a remote computer, comprising: (a) configuring a mobile system comprising a shipping container so that a multiplicity of ducted propeller units are in retracted positions and a local positioning system comprising a video camera and a laser range meter is in a retracted position in a shipping configuration; (b) floating the mobile system in the shipping configuration on a surface of a body of liquid; (c) establishing a communication channel between a computer system inside the shipping container and a remote computer via a wireless connection while the mobile system is floating; and (d) via the wireless connection, remotely activating a transformation of the mobile system from the shipping configuration to a deployed configuration in which the ducted propeller units and the local positioning system are in respective extended positions.

In accordance with one embodiment, the method described in the preceding paragraph further comprises: via the wireless connection, remotely controlling rotation of each ducted propeller unit to cause the mobile system in the deployed configuration to float to a location in proximity to a target object; acquiring linear acceleration and rotational rate data using an inertial measurement system that is fixed relative to the shipping container as the mobile system floats to the location; using the linear acceleration and rotational rate data from the inertial measurement system and a dead reckoning algorithm to compute an estimate of the position and orientation (i.e., location) of the shipping container; remotely activating the laser range meter to measure a distance to a point of interest on a surface of the target object; and remotely activating the video camera to capture an image of an area on the surface of the target object.

Other aspects of self-powered, self-contained mobile standoff measurement and inspection systems that can be teleoperated from a remote computer are disclosed below.

BRIEF DESCRIPTION OF THE DRAWINGS

The features, functions and advantages discussed in the preceding section can be achieved independently in various embodiments or may be combined in yet other embodiments. Various embodiments will be hereinafter described with reference to drawings for the purpose of illustrating the above-described and other aspects. None of the diagrams briefly described in this section are drawn to scale.

Reference will hereinafter be made to the drawings in which similar elements in different drawings bear the same reference numerals.

DETAILED DESCRIPTION

Figure 1:
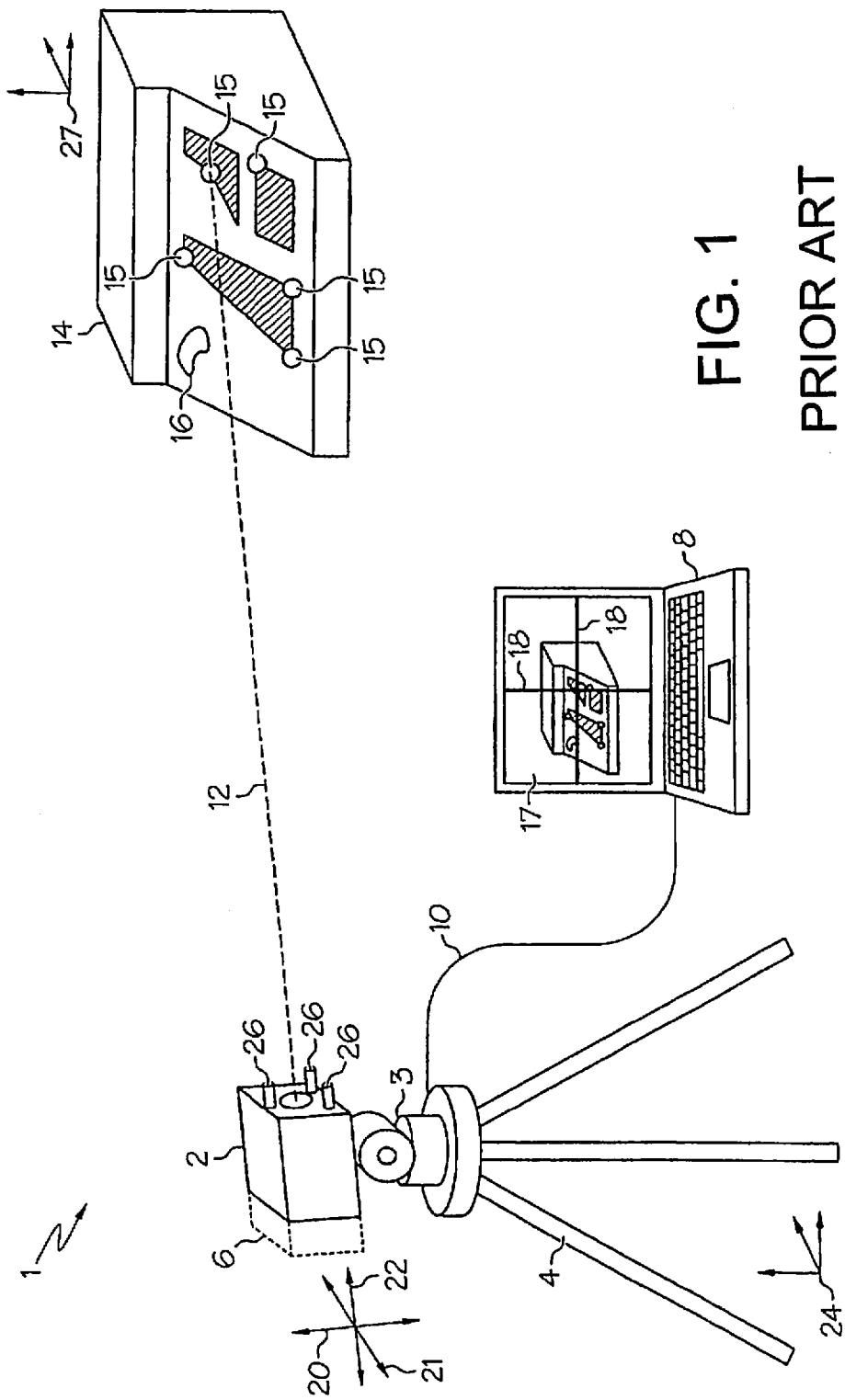
FIG. 1 is a diagram showing an orthographic view of a known (not mobile) local positioning system.

For the purpose of illustration, mobile stand-off measurement and inspection systems which can be operated by a remote expert at an operations center will now be described in some detail. However, not all features of an actual implementation are described in this specification. A person skilled in the art will appreciate that in the development of any such embodiment, numerous implementation-specific decisions must be made to achieve the developer's specific goals, such as compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure.

The distributed systems disclosed herein enable operation of one or more data collection devices from an off-site location without assistance from on-site personnel. Each system comprises a self-contained, remotely operable, mobile system that can be utilized to acquire three-dimensional measurement and two-dimensional image data in accurately registered three-dimensional coordinates. Each self-powered mobile stand-off measurement and inspection system can be operated by an NDI expert at a remote operations center. The on-site system can be utilized to inspect a large target object to determine precise locations in the coordinate system of the target object, and then locate areas or parts of interest within the operating region. The system comprises a mobile platform that allows the off-site NDI expert (or other operator) to drive the instrumentation to the inspection area without requiring any on-site setup. The communications between the system and the off-site operator can use a wired or wireless network connection. The mobile stand-off measurement and inspection system has on-board power; and when combined with wireless communications, the system can operate untethered.

For situations were the inspection equipment is shipped to a location and then returned, a variation in which the system is integrated into a shipping container can be used. When this system arrives at the inspection site it can connect to the wireless network, perform a systems check, and then when triggered by the off-site operator, transform into a configuration for mobile operation and stand-off inspection.

The distributed system with remotely operable stand-off inspection units disclosed herein leverages existing local coordinate measurement and remote operation techniques, specifically the capabilities of the local positioning systems described U.S. Pat. Nos. 9,285,296, 8,447,805 and 7,859,655. The non-mobile remote measurement and three-dimensional CAD integration aspects are disclosed in U.S. Pat. No. 9,182,487. The image data acquired by the video camera of the local positioning system may undergo image processing as disclosed in U.S. Pat. No. 8,744,133. Alternatively, the remotely operable stand-off inspection units may be equipped with one or more stand-off NDI sensors of the types disclosed in U.S. Pat. No. 9,285,296. The stand-off NDI technique employed can be selected from the following group: near-infrared spectroscopy, terahertz imaging, microwave imaging, x-ray backscatter imaging, stand-off infrared thermography, laser shearography, laser ultrasonic testing and laser vibrometry.

FIG. 1 depicts one embodiment of a local positioning system 1 suitable for providing position data on a target object 14 defined in the local coordinate system of the target object 14. The local positioning system 1 may comprise a video camera 2 having automated (remotely controlled) zoom capabilities. The video camera 2 may additionally include an integral crosshair generator to facilitate precise locating of a point within an optical image field display 17 for displaying video camera output on a personal computer or other display device 8. In applications in which the crosshair generator is not an integral component of the video camera 2, a crosshair generator 6 (shown in phantom) may be connected to the video camera 2 as a separate element for this purpose or overlaid on the video stream on the personal computer or display device 8.

The video camera 2 shown in FIG. 1 (and also seen in FIG. 2, discussed later) is coupled to a motion-controlled pan-tilt mechanism 3 mounted on a stationary tripod support 4. The motion-controlled pan-tilt mechanism 3 may be capable of rotationally adjusting the video camera 2 to selected angles around the vertical, azimuth (pan) axis 20 and the horizontal, elevation (tilt) axis 21, as well as rotation of the video camera 2 to selected angles about a roll camera axis 22. For the implementation discussed here, measurement and control of the roll axis is not required.

Still referring to FIG. 1, a direction vector that describes the orientation of the video camera 2 relative to a fixed coordinate system 24 of the tripod 4 (or other platform on which the pan-tilt unit is attached) is determined from the azimuth and elevation angles, as well as the position of the center of the crosshair marker in the optical field when the video camera 2 is aimed at a point of interest 16 on the target object 14. In FIG. 1, the aim direction vector 12 is represented by a line which extends from the lens of camera 2 and intersects a location 15 on target object 14.

The specific implementation shown in FIG. 1 includes a plurality (e.g., three) of laser pointers 26 mounted on the camera 2 and aligned with the aim direction vector 12. Laser pointers 26 can be used to provide a visual indication on the target object 14 as to the aim or direction of the video camera 2. In an alternative embodiment (not shown in FIG. 1, but see FIG. 2), a laser range meter 25 may be incorporated into the camera unit, which laser range meter 25 can also perform the function of a laser pointer.

In the embodiment of a non-mobile local positioning system 1 shown in FIG. 1, the video camera 2 and pan-tilt mechanism 3 are operated by a personal computer or other computer (hereinafter "computer 8"). The computer 8 communicates with video camera 2 and pan-tilt mechanism 3 through a video/control cable 10. The angular positions of the pan and tilt units of the pan-tilt mechanism 3 (and therefore the orientation of the video camera 2) can be controlled using the keyboard of computer 8 or some other input device. The optical image field display 17, with crosshair overlay 18, as sighted by the video camera 2, can be displayed on the monitor of computer 8.

The local positioning system 1 shown in FIG. 1 further comprises three-dimensional localization software which is loaded into computer 8. For example, the three-dimensional localization software may be of a type that uses multiple calibration points 15 on the target object 14 (such as points or features on a surface on an aircraft) to define the location (position and orientation) of video camera 2 relative to target object 14. The calibration points 15 may be visible features of known position (such as the corner of a window frame, a screw used to attach the pitot tube, etc.) in the local coordinate system 27 of the target object 14 as determined from a three-dimensional database of feature positions (e.g., a CAD model) or other measurement technique. During the LPS calibration process, X,Y,Z data for at least three non-collinear points are extracted from the CAD model. Typically calibration points are selected which correspond to features that can be easily located on the target object. The three-dimensional localization software utilizes the calibration points and the pan and tilt data from the pan-tilt mechanism 3 to define the relative position and orientation of the video camera 2 with respect to the local coordinate system 27 of the target object 14 (described in more detail below). The measured distances to the calibration points 15 may be used in coordination with the azimuth and elevation angles from the pan-tilt mechanism 3 to solve for the camera position and orientation relative to the target object 14.

Although the local positioning system 1 shown in FIG. 1 is not mobile, the methodology for determining the position and orientation of a video camera (or other measurement instruments) mounted on a pan-tilt mechanism relative to a target object is equally applicable to a local positioning system incorporated in a mobile telepresence platform. Further details concerning this methodology, e.g., how to generate a camera pose transformation matrix reflecting the position and orientation of a video camera (and attached measurement instruments) relative to a coordinate system of a target object, are set forth in the Appendix.

Once the position and orientation of the video camera 2 with respect to the target object 14 have been determined, the computer 8 may be operated to rotate and zoom the optical image field of the video camera 2 to a point of interest 16 of unknown coordinate position on the target object 14, which may be a damage/repair location on an aircraft, for example. At this position of the aim direction vector 12, the orientation of the video camera 2 (which may include the respective angles of the video camera 2 along the azimuth axis 20 and the elevation axis 21) may be recorded. By using the azimuth and elevation angles from the pan-tilt unit and the relative position and orientation of the video camera 2 determined in the calibration process, the location of the point of interest 16 can be determined relative to the coordinate system 27 of the target object 14. The damage/repair location 16 on the target object 14 may be sized by aligning the crosshairs 18 in the optical image field of the video camera 2 along the boundary of the damage/repair location. In the case of a crack, the length of the crack may be measured by moving the crosshairs from one tip of the crack to the other tip of the crack.

The reverse process, in which the position of a point of interest 16 may be known in the target object's coordinate system (from a previous data acquisition session, a CAD model, or other measurement), can also be performed. In this situation, the camera may be placed in any location on the work area where calibration points are visible (which may be in a different location than the location where the original data was recorded) and the instrument-to-target calibration step may be performed. This calibration is referred to herein as "the camera pose", but it is associated with more than just the camera; for example, it may also include instrumentation for measuring distance (such as a laser range meter). The aim direction vector 12 from the point of interest 16 to the video camera 2 may be calculated in the target object's coordinate system 27. The inverse of the camera pose transformation matrix may be used to convert the aim direction vector 12 into the coordinate system of the video camera 2. The azimuth and elevation angles may then be calculated and used by the pan-tilt unit to aim the video camera 2 at the point of interest on the target object 14.

In a typical implementation, the LPS instrument may be set up within about 10-50 feet of the target object 14. The target object 14 may, for example, be a structure such as a storage tank or a large vehicle such as an aircraft. The calibration points 15 on the target object 14 may be selected and used by the three-dimensional localization software (loaded in computer 8) in conjunction with the pan and tilt data (i.e., azimuth and elevation angles) from the pan-tilt mechanism 3 to determine the position and orientation of the video camera 2 with respect to target object 14. The calibration points 15 may be feature points of known position in the local coordinate system 27 of the target object 14 as determined from a three-dimensional CAD model or other measurement technique. In some implementations, the pan-tilt unit 3 may be attached to a portable support such as a tripod 4. In other implementations, the pan-tilt unit could be attached to a stationary support, such as the walls of an airplane hangar.

The three-dimensional localization software loaded onto the computer 8 can be utilized to determine the position and orientation of the video camera 2 with respect to the target object 14 and generate a camera pose transformation matrix using one of three known methods: (1) a vector-based approach; (2) position and orientation based on five- or seven-point technique; and (3) a laser range-based system. The vector-based approach may utilize three calibration points 15 on the target object 14 and solve simultaneous equations to determine the position of the video camera 2 with respect to the target object 14. This assumes the relative orientation of the camera is known. The position and orientation calibration based on five- or seven-point techniques may determine both the position (X,Y,Z) and the orientation (roll, pitch, yaw) of the video camera 2 relative to the target object 14. The five-point method may utilize five known calibration points 15 that all lie on the same planar surface of the target object 14. The seven-point method may utilize seven known calibration points 15 that are not all on the same planar surface of the target object 14.

Optionally, an off-the-shelf laser-based distance measurement device, such as a laser range meter (also called "a laser range finder" and "laser distance meter") may be integrated into the video camera 2 to create a laser hybrid system. This laser range meter/video camera hybrid system may be incorporated onto the pan-tilt mechanism 3. Measurement data from the laser range meter can be used to obtain estimates of the respective distances from the laser range meter (i.e., from the video camera) to calibration points on a target object. A typical laser range meter comprises a laser diode which transmits a bundled, usually visible, laser beam toward a surface of a target object. The light which is backscattered and/or reflected by the target object is imaged on the active surface of a photoreceiver by receiving optics. The laser diode has a position and an orientation which are fixed relative to the position and orientation of the video camera; the photoreceiver has a position and an orientation which are fixed relative to the position and orientation of the laser diode. The time-of-flight between transmission and reception of the light can be used to calculate the distance between the laser range meter and the portion of the target object surface on which the transmitted beam impinged. The laser range meter also functions as a laser pointer. Alternatively, a distance meter which directionally projects wave energy other than a laser beam could be utilized.

Figure 2:
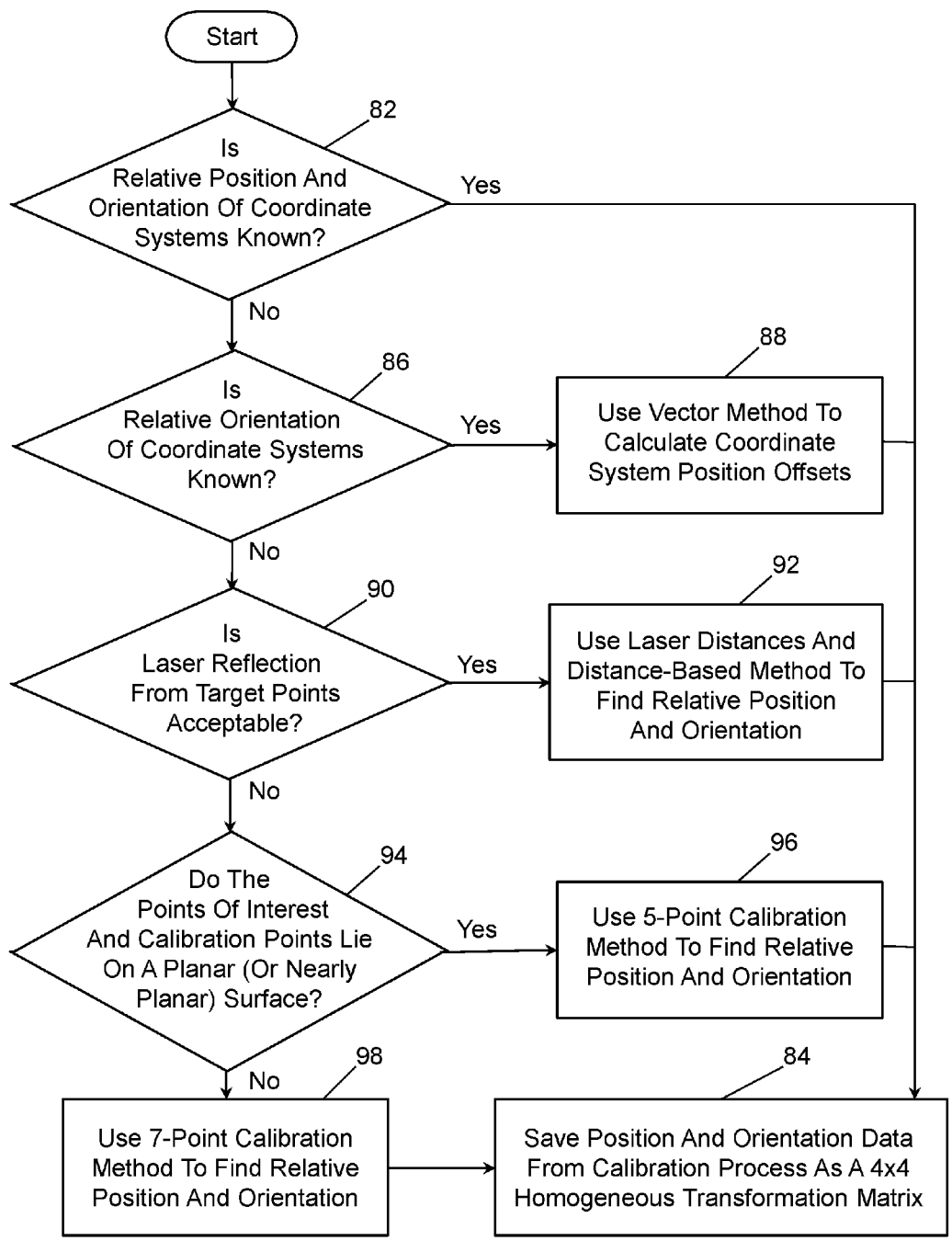
FIG. 2 is a flowchart showing steps of a method for generating an instrument to target calibration transformation matrix (sometimes referred to as the camera pose) in accordance with one embodiment, which method can be utilized by both mobile and non-mobile local positioning systems.

FIG. 2 is a flowchart showing steps of a method for generating a camera pose transformation matrix in accordance with one embodiment, which method can be utilized by both mobile and non-mobile local positioning systems. In step 82, a determination is made whether the relative position and orientation of the coordinate systems of the video camera and the target object are known or not. If the decision made in step 82 is affirmative, then the position and orientation data from the calibration process is saved as a 4×4 homogeneous transformation matrix in step 84.

If the decision made in step 82 is negative (i.e., at least one of the relative position and relative orientation of the coordinate systems is unknown), then a determination is made in step 82 whether the relative orientation of the coordinate systems is known or not. If the decision made in step 86 is affirmative (i.e., the relative orientation of the coordinate systems is known), then a vector method (step 88) may be used to calculate coordinate system position offsets. The position and orientation data derived from the calibration process in step 88 are then saved as a 4×4 homogeneous transformation matrix (step 84).

If the decision made in step 86 is negative (i.e., the relative orientation of the coordinate systems is not known), then a determination is made in step 90 whether laser reflections from the calibration points on the target object are acceptable or not. If the decision made in step 90 is affirmative (i.e., the laser reflections from the calibration points on the target object are acceptable), then the laser distances and a distance-based method may be used (step 92) to calculate the position and orientation of the camera relative to the target object (i.e., calculate the position and orientation of the coordinate system of the camera relative to the coordinate system of the target object. The position and orientation data derived from the calibration process in step 92 are then saved as a 4×4 homogeneous transformation matrix (step 84).

If the decision made in step 90 is negative (i.e., the laser reflections from the calibration points on the target object are not acceptable), then a determination is made in step 94 whether the calibration points and the points of interest lie on a planar or nearly planar surface or not. If the decision made in step 94 is affirmative (i.e., the calibration points and the points of interest lie on a planar or nearly planar surface), then a five-point calibration method (step 96) is used to calculate the position and orientation of the camera relative to the target object. The position and orientation data derived from the calibration process in step 96 are then saved as a 4×4 homogeneous transformation matrix (step 84).

If the decision made in step 94 is negative (i.e., the calibration points and the points of interest do not lie on a planar or nearly planar surface), then a seven-point calibration method (step 98) is used to calculate the position and orientation of the camera relative to the target object. The position and orientation data derived from the calibration process in step 98 are then saved as a 4×4 homogeneous transformation matrix (step 84).

Returning to FIG. 1, once the position and orientation of the video camera 2 with respect to the target object 14 have been determined and the camera pose transformation matrix has been generated, camera pan data (angle of rotation of video camera 2 about the azimuth axis 20) and tilt data (angle of rotation of video camera 2 with respect to the elevation axis 21) may be used in conjunction with the calculated position and orientation of video camera 2 to determine the (X,Y,Z) position of any point of interest (such as the damage/repair location on the skin of the aircraft) in the coordinate system of the target object 14. The video camera 2 may then be aimed at the damage/repair location on the target object 14, with the center and/or outline of the damage/repair location defined.

Because the position of the damage/repair location on the target object 14 may initially not be known, the pan and tilt angles of the pan-tilt mechanism 3 may be used to determine the aim direction vector 12 in the local camera coordinate system 24 of the video camera 2. Determination of the surface position of the damage/repair location may be made by any one of the following methods: (1) an approximation using the ray intersection from a polygonal surface formed from the calibration points, or other user-selected features of known position on the target object; (2) three-dimensional data from a CAD model, for example; or (3) the distance from the optional laser-based measurement device. At this stage, the camera pose transformation matrix may be used to transform or convert the damage/repair location, which is initially defined in the local coordinate system of video camera 2, into the local coordinate system 27 of target object 14.

A three-dimensional model coordinate system and maintenance database of the target object 14 may then be accessed by computer 8 to locate previous locations of damage, repairs and/or other issues on the target object 14. Present repair of the damage/repair location on the target object 14 may then be planned and completed based on the positional and geometric relationships of the previous damage, repairs and/or issues with the damage/repair location. The positional and geometric information of the video camera 2 when its optical image field is aimed at the damage/repair location may be saved and superimposed on the three-dimensional model, which may be maintained in a database. Digital photographs of the damage/repair location may additionally be taken using the video camera 2 or other camera and saved in the database. Accordingly, the updated database is available in the event that a subsequent repair of the target object 14 is called for.

Figure 3:
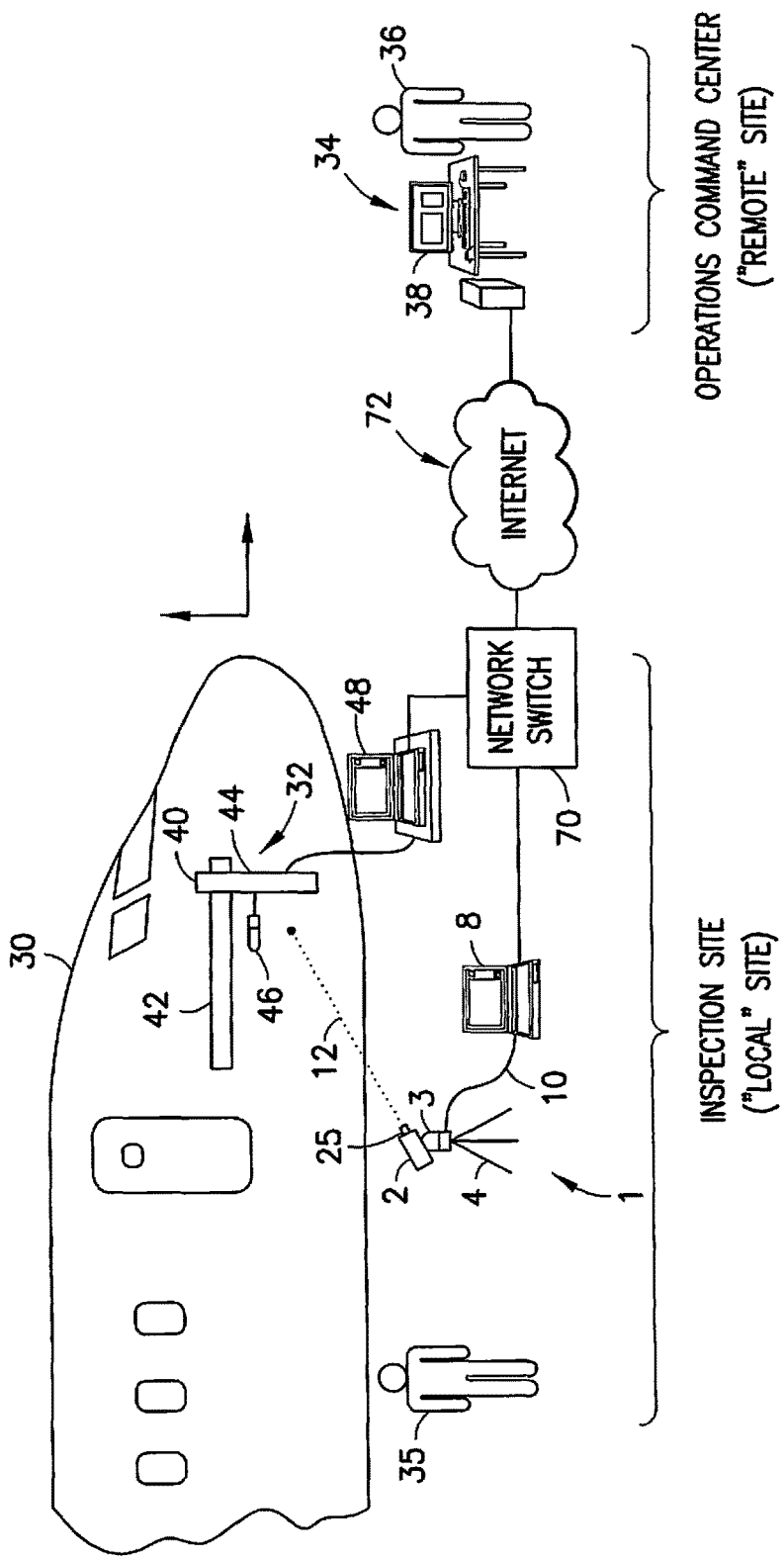
FIG. 3 is a diagram showing components of a distributed system for measuring and inspecting an aircraft at a local site, as disclosed in U.S. patent application Ser. No. 13/166,613. The inspection system combines a stand-off local positioning system positioned adjacent to an aircraft at the inspection site with an NDI scanner mounted to the target object, which systems are set up with the assistance of on-site personnel.

FIG. 3 shows an acquisition and analysis system for non-destructive inspection employing multiple hardware and software components (including a local positioning system) networked through a central analysis interface. (The local positioning system 1 shown in FIG. 3 may be of the type previously described with reference to FIGS. 1 and 2.) The integration of these components enables a remote operator to acquire and analyze NDI data using automated scanning equipment and local positioning system 1, and then visualize and interact with the data using two- and three-dimensional analysis software. Alignment points measured by the local positioning system 1 in the scanning area are used to create a positional correspondence for setup of the scanning equipment and registering the resulting two-dimensional scan data in the coordinate system of a three-dimensional CAD model visualization environment. The ability to operate all of the hardware and software components remotely enables data collection by an expert NDI analyst 36 located at an off-site operations center, with the only on-site assistance coming from non-expert support personnel (e.g., a support technician 35) to setup the LPS and NDI scanning hardware.

The primary on-site and off-site hardware components of the system shown in FIG. 3 will now be described. A local positioning system 1 for determining local three-dimensional coordinates of an aircraft 30 and an NDI scanner 32 are located at the inspection site (referred to herein as the "local site"). A remote computer 34 (e.g., a command workstation), operated by an NDI expert 36, is located at an operations command center (referred to herein as the "remote site") with a master display 38. The NDI scanner 32 comprises a scanning unit 40 having a support rail 42 mounted on the aircraft and a translation rail 44 supporting an ultrasonic head 46. The translation rail 44 moves along the support rail 42 for a first scan axis and the head 46 moves along the translation rail 44 for a second scan axis, which can be perpendicular to the first scan axis. The NDI scanning unit is controlled by a second control PC 48.

For conducting remote NDI operations, tasks performed by a support technician 35 at the inspection site include: removing the local positioning system 1 and NDI scanner 32 from shipping/storage containers; setting up the local positioning system 1; attaching the NDI scanner 32 to the aircraft 30; and connecting the control personal computers 8 and 48 to the Internet 72 by way of a network switch 70. The Internet connection of the control personal computers 8 and 48 may be wired or wireless. After setup, the local positioning system 1 allows an NDI expert 36 at the remote site to help guide the rest of the process, as will be described in greater detail hereinafter. Once the control personal computer 8 is started, an automated process will send the on-site network domain information back to the operations center via network switch 70 and the Internet 72.

The NDI scanning aspects of the system shown in FIG. 3 are not germane to the mobile stand-off inspection system that will be disclosed in detail later with reference to FIGS. 4 through 7, but the local positioning aspects of the system shown in FIG. 3 are germane and will be described in further detail hereinafter.

Still referring to FIG. 3, when the on-site setup of the local positioning system 1 has been completed by the on-site support technician 35, the NDI expert 36 at the operations center connects to the LPS control personal computer 8 through a network socket connection (not shown) in the remote computer 34 to operate a video camera 2, a pan-tilt mechanism 3 and a laser range meter 25 (which can also function as a laser pointer) using an LPS graphical user interface (GUI) (not shown) and a manual controller (not shown). A video connection is also established through an LPS video server (not shown). The visual display of the LPS GUI and associated video from the local positioning system 1 are displayed on the master display 38. The LPS GUI allows communication of position data as well as camera/video data from the local positioning system 1 to the remote computer 34, and control of the local positioning system 1 for positioning, orientation and operation of video camera 2 and laser range meter 25 from the remote computer 34.

The ease-of-use of the measurement and inspection system shown in FIG. 3 can be improved by employing a stand-off (i.e., non-contact) NDI system instead of a contact-type NDI system and by substituting a mobile local positioning system for a stationary system, as described in more detail below.

Figure 4:
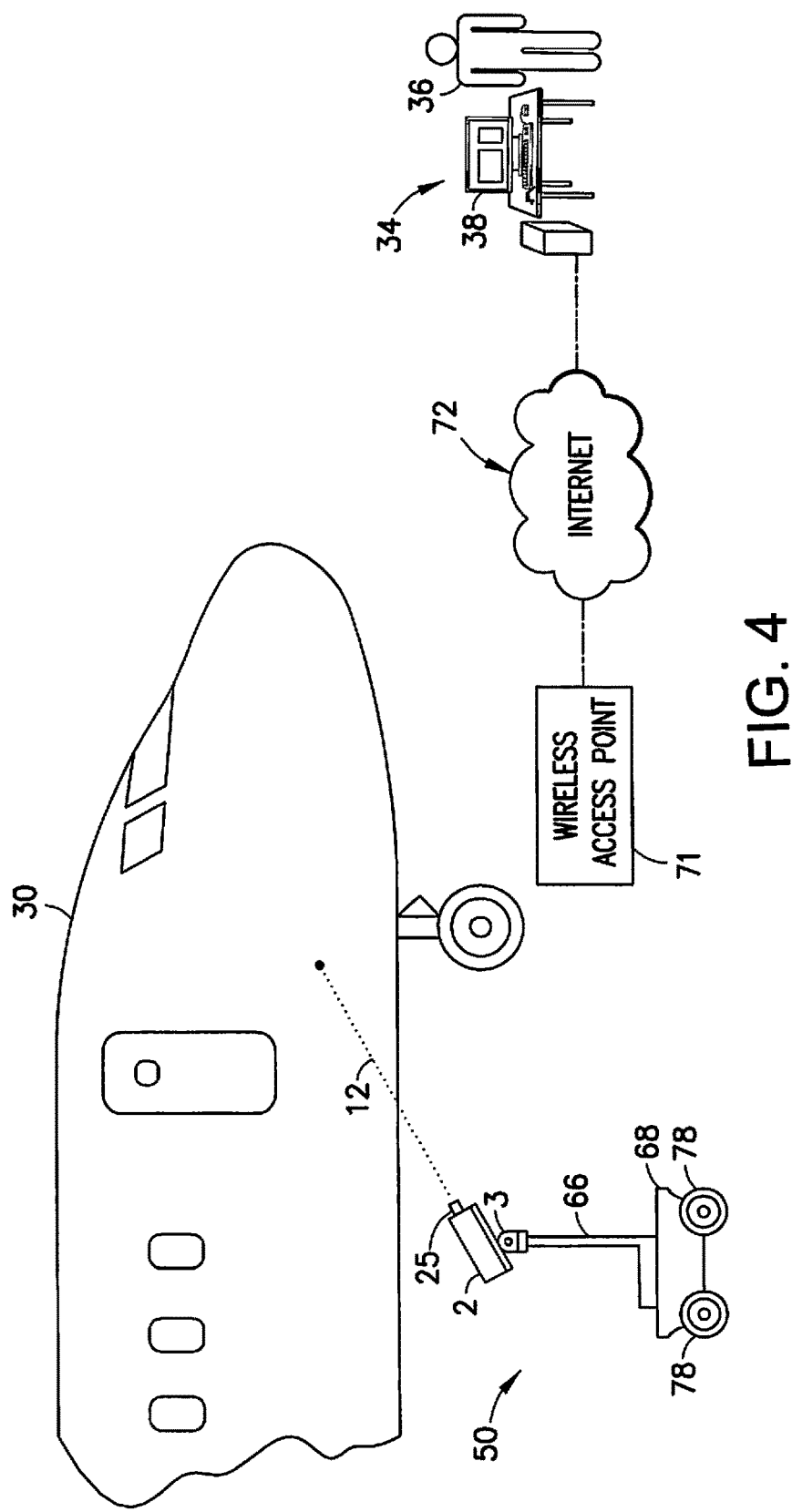
FIG. 4 is a diagram showing components of a distributed system for stand-off measurement and inspection of an aircraft at a site distant from an operations center of a distributed inspection system with minimal on-site personnel assistance.

FIG. 4 shows components of a distributed system for stand-off measurement and inspection of an aircraft 30 at a site distant from an operations command center with minimal on-site personnel assistance. This expanded implementation of the distributed system comprises a battery-powered mobile standoff measurement and inspection system 50 situated on the ground at the inspection site. In accordance with the embodiment depicted in FIG. 4, mobile standoff measurement and inspection system 50 combines a mobile platform 68 having four wheels 78 (only two of which are visible) with an LPS unit mounted to a vertical pole 66. The LPS unit comprises a video camera 2, a pan-tilt mechanism 3 and a laser range meter 25 of the types previously described. The mobile standoff measurement and inspection system 50 further comprises means (not shown in FIG. 4) for communicating with a wireless network access point 71, which in turn enables communication with a remote computer 34 at an operations command center via the Internet 72. Movement of the platform 68 and operation of the LPS unit can be controlled remotely by an NDI expert 36 situated at the operations command center. The components can be controlled by a wireless connection, or by tethered connection if necessary. Optionally, the mobile standoff measurement and inspection system may be collapsible for shipping purposes, in which case the system may be provided with one or more deployment actuators that can be operated under the control of the NDI expert at the operations command center. The system components may be ruggedized to withstand the rigors of shipping.

Because the mobile standoff measurement and inspection system 50 shown in FIG. 4 can be operated remotely, it can be controlled by an off-site NDI expert 36 with minimal on-site support. The tasks performed at the inspection site include receiving the mobile standoff measurement and inspection system 50 from a shipping company, moving the mobile standoff measurement and inspection system to or closer to the inspection site, and making sure that there is a relatively clear path for the mobile system to access the airplane. The ability to set up the system by commands sent via wireless communication allows an off-site NDI expert 36 to perform inspection and measurement of the aircraft 30 without requiring on-site personnel to setup the inspection equipment. The off-site NDI expert 36 can also provide guidance to an on-site repair team using the laser range meter 25 as a laser pointer, as well as using integrated audio and display capabilities on the mobile platform.

The ability to communicate with and control the operation of the mobile standoff measurement and inspection system provides a telepresence platform that allows the off-site NDI expert 36 to explore the inspection environment and use the on-board LPS capabilities to acquire position measurements in either a point-to-point form or in Cartesian coordinates of the local coordinate system of the target object (in this case, an aircraft 30). Additional two-way audio and display components may be added to the mobile standoff measurement and inspection system to extend the functionality to that of a full telepresence platform capable of performing measurements.

The mobile standoff measurement and inspection system 50 can be used to determine the exact position of an in-service NDI scan in airplane coordinates and then the NDI expert 36 can use that information to retrieve the exact CAD data that matches the stand-off NDI scan, and then provide an overlay of the underlying airplane structure on top of the NDI image using the airplane CAD data.

The mobility of the platform enables the acquisition of measurements defined in terms of the local coordinate system of the target object with the freedom to move the measurement system around at the inspection site. The ability to acquire measurements from a mobile platform is an important capability for off-site inspectors and maintenance personnel, and also as a tool for designers and managers for initial manufacturing.

The mobile platform 68 may be a holonomic motion vehicle. The vehicle may also have an on-board position and orientation tracking system that may comprise a set of omni wheels arranged in a four-omni wheel, perpendicular, double-differential odometry configuration of the type disclosed in U.S. Pat. No. 9,470,658. Adding a real-time tracking system, such as multi-axis odometry, to the mobile platform allows the system to be controlled at a higher level, such as by instructing it to move to specific coordinates instead of requiring the remote operator to drive the platform directly. This also enables the mobile platform to be programmed to automatically follow a specified path plan, which may include returning to a specific location where prior LPS measurements or images were recorded. Even if the tracking system could only produce a rough estimate, measurements made by the mobile local positioning system could be used to determine a more accurate location of the platform relative to the target object.

As with other mobile telepresence systems, a mobile platform, camera, microphone, and speaker can part of the full system. On-board lighting and environmental sensors, such as weather station sensors (temperature, humidity, wind speed) or proximity sensors (for collision avoidance), may also be included on the mobile platform. Additional inspection sensors, such as the stand-off NDI sensors disclosed in U.S. Pat. No. 9,285,296, may also be part of a mobile measurement and inspection system. In these cases, NDI, measurement, telepresence and guidance capabilities enables the entire inspection to be accomplished remotely.

Figure 5:
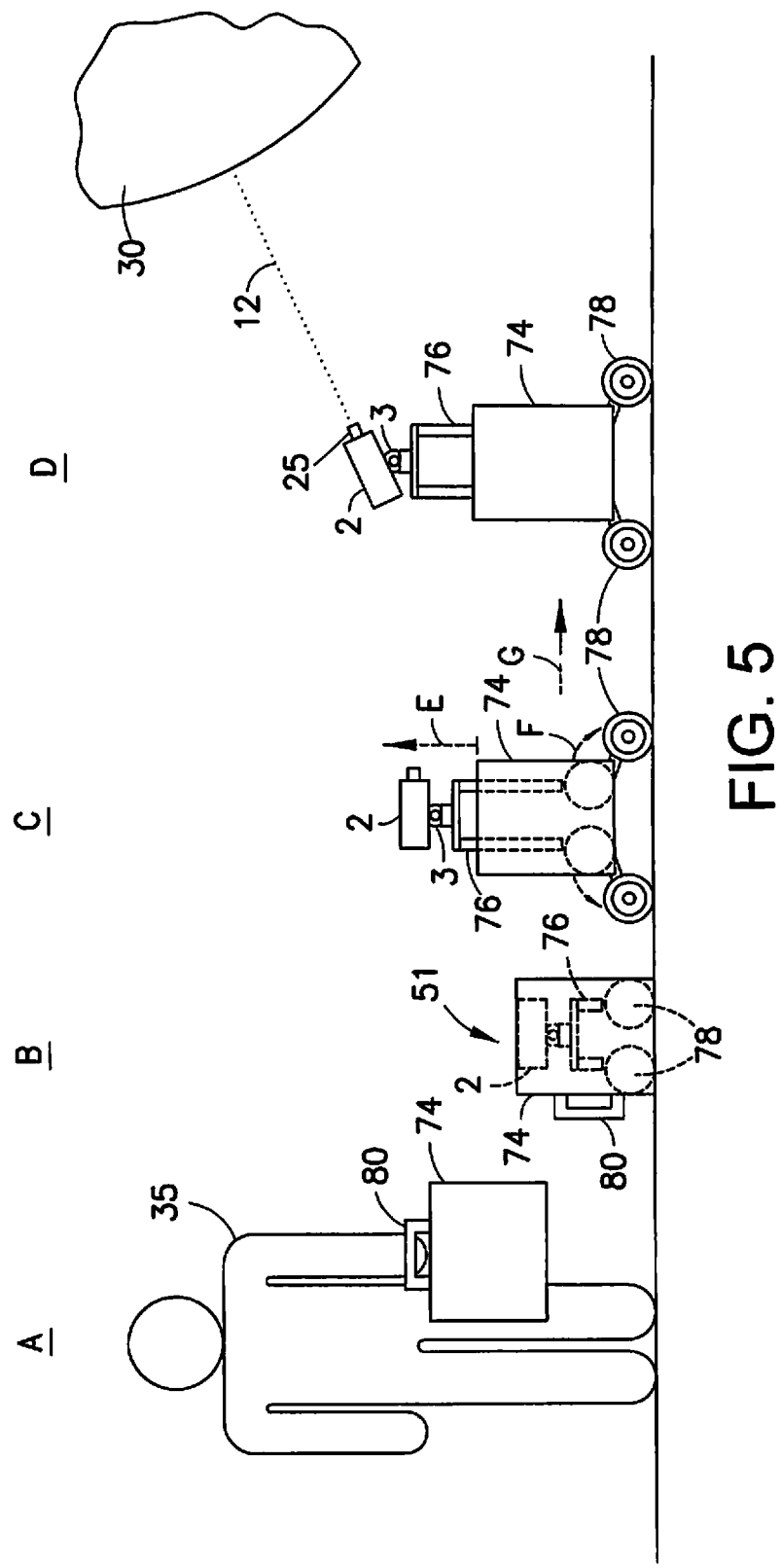
FIG. 5 is a diagram showing three configurations of a self-contained, remotely operable, mobile standoff measurement and inspection system for stand-off inspection of large target objects in accordance with one on-site usage scenario.

In some situations where the mobile standoff measurement and inspection system is shipped to the inspection site, it can be useful to package all of the on-site inspection components into a single, reusable shipping container. One example of such a self-contained mobile standoff measurement system is shown in FIG. 5. Having the inspection system integrated with a shipping container 74 has the advantage that the on-site technician 35 need not unpack components from the container or re-pack them when the inspection is complete. The shipping container 74 serves as a protective shell during shipment for the systems components, including deployable components intended to contact or interact with the environment at the inspection site. The shipping container may comprise motorized doors which open to allow extension of the deployable components and reclose after retraction of those same components. Additional display elements may be integrated into the exterior of the container, such as an integrated electronic label (i.e., an externally visible display that uses electronic ink) that can be used to show shipping information on the exterior of the container. This can be changed remotely to provide the destination information for return shipment.

The self-contained, remotely operable, mobile standoff measurement and inspection system (hereinafter "mobile measurement and inspection system 51") shown in FIG. 5 comprises a shipping container 74 and various deployable subassemblies which fit inside the container when retracted and protrude outside the container when extended. These subassemblies can be deployed in response to commands received, from an NDI expert 36 at the operations command center.

FIG. 5 shows three configurations of the mobile measurement and inspection system 51 for stand-off inspection of large target objects in accordance with one on-site usage scenario. For this example, the video camera 2 will perform the stand-off inspection function (such as the functionality disclosed in U.S. Pat. No. 8,744,133). The configurations shown in FIG. 5 would also be applicable to mobile inspection systems that used other types of stand-off NDI sensor units.

FIG. 5 depicts four stages A through D which occur successively over time at the inspection site. Part A of FIG. 5 shows a support technician 35 carrying a self-contained mobile measurement and inspection system 51 to or toward the inspection site. In the implementation shown, self-contained mobile measurement and inspection system 51 comprises a container 74 with a handle 80.

Figure 6:
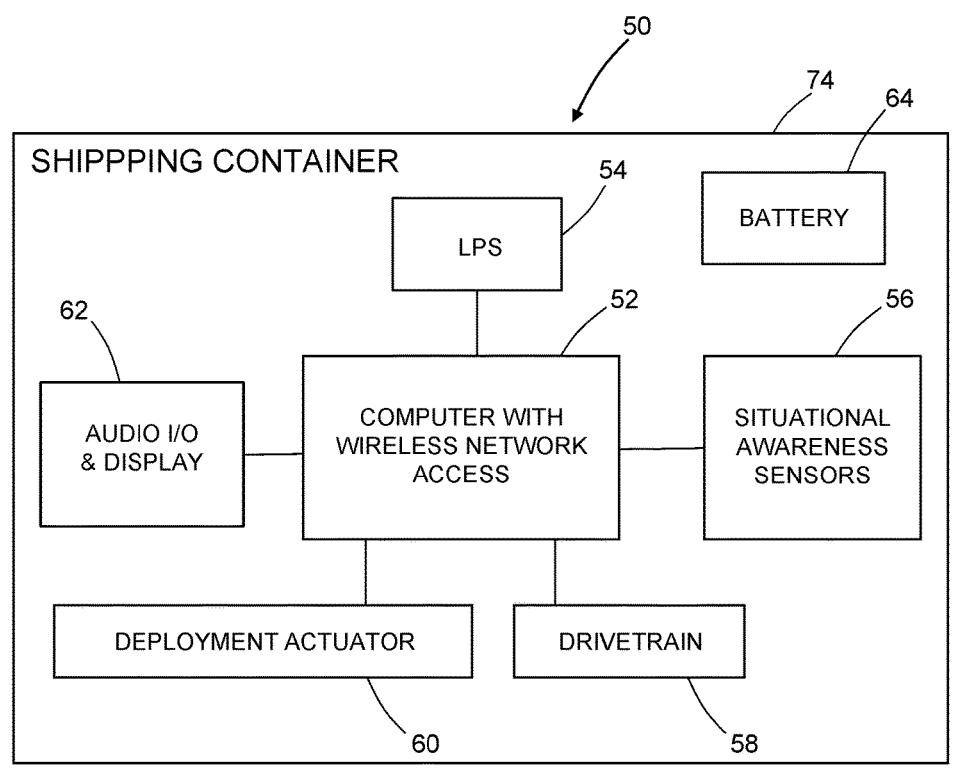
FIG. 6 is a diagram showing hardware and software components of a self-contained, remotely operable, mobile standoff measurement and inspection system for stand-off inspection of target objects in accordance with one embodiment.

Other system components are disposed inside the container 74 when the system is in its shipping configuration. FIG. 6 shows the following internal components: a computer 52 with wireless network access (e.g., via an internal or external wireless adapter); an LPS unit 54 that communicates with computer 52; situational awareness sensors 56 which communicate with computer 52; a drivetrain 58 comprising at least one actuator (such as an electric motor) which communicates with computer 52; deployment subsystem 60 comprising at least one actuator which communicates with computer 52; and audio input/output and display units 62 which communicate with computer 52. All electrical devices are powered by an electrical power source, such as a battery 64.

Returning to FIG. 5, Part B shows the self-contained mobile measurement and inspection system 51 (partly depicted in FIG. 6) in its retracted configuration after the technician 35 has placed the system on the ground. The container 74 may be provided with marking to indicate which face should be placed in contact with the ground for proper pre-deployment placement. For proper deployment, the self-contained mobile measurement and inspection system 51 must be placed upright with wheels 78 under the LPS unit (see item 54 in FIG. 6). After the technician has placed the self-contained mobile measurement and inspection system 51 at a desired location, the technician has no further role to play until the automated inspection has been completed and the system is destined to be shipped back to the operations command center (or other warehousing location).

The NDI expert at the operations command center has the ability to send commands to the on-board computer of the mobile standoff measurement and inspection system. To activate deployment, the NDI expert sends a command which causes the on-board computer to activate the one or more deployment actuators to cause extension (by translation and/or rotation) of the deployable components. As a result of these motions, the system adopts a measurement configuration in which the deployable components (e.g., video camera, laser range meter, and wheels) extend out of the shipping container 74. Part C of FIG. 5 shows the self-contained mobile measurement and inspection system 51 during extension of the deployable components. The vertical dashed arrow E indicates that LPS unit is being extended upward; the curved dashed arrows F indicate that wheels 78 are being pivoted outward in opposite directions along respective arcs.

As best seen in Part C of FIG. 5, one deployable subassembly of the mobile standoff measurement and inspection system comprises the LPS unit (including video camera 2 mounted to pan-tilt mechanism 3) and an extendible/retractable support frame 76 (shown in an extended state in FIG. 5) to which the pan-tilt mechanism 3 is attached. When support frame 76 is retracted, the video camera 2 and pan-tilt mechanism 3 will be housed inside the container 74. The support frame 76 may comprise a pair of telescoping arms. Alternatively, the extendible/retractable support frame 76 can be slidably coupled to a container frame (a rigid internal part of the shipping container 74) in a well-known manner (e.g., by means of linear guide halves respectively mounted to the support frame 76 and the container frame). In one implementation, a linear deployment actuator (not shown in FIG. 5) is installed inside the container 74. For example, the linear actuator may comprise a lead screw (not shown) threadably coupled to a lead screw nut (not shown) that is attached to the support frame 76, so that the latter extends or retracts depending on the direction in which the lead screw is rotated. The lead screw can be coupled to the output shaft of an electric motor (not shown), also housed inside the container 74. Other types of electromechanical linear actuators, capable of being powered by a battery, can be used.

Another deployable subassembly, which fits inside the container 74 when retracted and protrudes outside the container 74 when extended, comprises four wheels 78 (only two of which are visible in FIG. 5) and associated mechanisms (e.g., wheel axles, rotary encoders, etc.). At least one of the wheels 78 is a drive wheel that receives torque from the drivetrain and provides the final driving force for the mobile standoff measurement and inspection system. Each wheel 78 may be mounted to a respective axle which is pivotably mounted at a distal end of a respective deployable arm (not shown). In accordance with one implementation, four deployable arms may be coupled together so that they all rotate in unison in response to activation of an actuator. In one implementation, a rotary deployment actuator (not shown in FIG. 5) is installed inside the container 74. For example, the rotary actuator may comprise a set of gears (not shown), including respective gears mounted to each axle, one gear mounted to the output shaft of an electric motor (not shown), and other intervening gears which couple the axle-mounted gears to the shaft-mounted gear. Other types of electromechanical rotary actuators, capable of being powered by a battery, can be used. In some embodiments (not shown in FIG. 5), a single actuator may be used to deploy both the LPS unit and the wheels using a mechanical linkage connecting both subsystems to the same actuator.

After the deployable components have been deployed (at which time the self-contained mobile measurement and inspection system 51 will be in its measurement configuration), the NDI expert sends a command which causes the on-board computer to activate the drivetrain to move the self-contained mobile measurement and inspection system 51 to a desired location. This movement is indicated by arrow G in FIG. 5. After the system has been positioned at the commanded location, the NDI expert can send commands to the on-board computer instructing the LPS unit to begin the calibration process.

The self-contained mobile measurement and inspection system 51 comprises on-board instrumentation capable of making dimensional measurements in the local coordinate system of the target object 14. More specifically, the on-board computer 52 (see FIG. 6) can be loaded with three-dimensional localization software of a type that uses multiple calibration points on the aircraft 30 (see FIG. 5) to define the location (position and orientation) of video camera 2 relative to aircraft 30. The calibration points may be visible features of known position (such as the corner of a window frame, a screw used to attach the pitot tube, etc.) in the local coordinate system of the aircraft 30 as determined from a three-dimensional database of feature positions (e.g., a CAD model) or other measurement technique.

Part D of FIG. 5 shows the mobile standoff measurement and inspection system in its measurement configuration as the LPS unit directs a laser beam at a calibration point on the aircraft 30. The three-dimensional localization software utilizes the calibration points (i.e., light reflected from the calibration points in response to impinging laser beams transmitted by the laser range meter of the LPS unit) and the pan and tilt data from the pan-tilt mechanism 3 to define the relative position and orientation of the video camera 2 with respect to the local coordinate system of the aircraft 30. The measured distances to the calibration points may be used in coordination with the azimuth and elevation angles from the pan-tilt mechanism 3 to solve for the camera position and orientation relative to the aircraft. The on-board computer may be further programmed to generate a camera pose transformation matrix reflecting the position and orientation of the video camera relative to the coordinate system of the aircraft.

In accordance with alternative embodiments, the three-dimensional localization software can be hosted on a computer at the operations command center, which computer receives distance and pan-tilt angle information from the mobile local positioning system for use in calculating a camera pose coordinate transformation matrix.

More specifically, there are two ways that the point measurement data for calibration can be acquired: (1) manual acquisition (teleoperation) and (2) automated acquisition (in which the LPS unit and processing software finds the calibration points itself).

(1) In the manual process, three non-collinear points are required for which the X,Y,Z positions are known and defined in the aircraft coordinate system. These points can come from any trusted source, for example: CAD data or prior measurement with another system. When CAD data is used, the NDI expert at the operations command center visually finds the points by selecting them in a CAD model visualization environment (or equivalently from data stored from a prior session), and saves the X,Y,Z data for each point (to a file or memory). With the LPS unit active and connected to the network, the images acquired by the video camera of the mobile local positioning system are sent back to the operations command center for viewing on the display screen of the remote computer. Then the NDI expert visually finds the same points on the aircraft by remotely controlling the direction in which the video camera of the mobile local positioning system is aimed and saves the pan, tilt, and distance measurements for each calibration point. Using the known and measured data, the calibration process (set forth in more detail in the Appendix) computes the 4×4 homogeneous transformation matrix that defines the position and orientation of the camera relative to the aircraft (sometimes called the "camera pose").

(2) For the automated process, the mobile local positioning system can use its on-board camera and image processing software in some conditions to find features on the aircraft and associate those features with their known three-dimensional data points. Automated feature tracking is possible using two-dimensional image processing software, in situations where the same high-contrast calibration points that were initially selected by the NDI expert are continuously visible during movement of the local positioning system to a new location, then those two-dimensional image features can be used to direct the local positioning system to acquire new three-dimensional points using those two-dimensional locations (which are converted into pan and tilt angles for local positioning system aiming, and then laser distance acquisition). The on-board computer of the mobile local positioning system can then use the acquired data to compute a new camera pose transformation matrix. If the motion of the mobile local positioning system is too large for the same calibration features to remain visible throughout the motion path to the new location, the system can signal the NDI expert at the operations command center that manual recalibration is required. To minimize the distance that the mobile local positioning system will travel during the automated calibration process, preferably before the latter process is started, the NDI expert will drive the mobile local positioning system to a location near to location whereat the inspection will be performed. In order for the automated process to work, the local positioning system should be manually calibrated once at the start (i.e., an initial calibration). Thereafter computer on board the mobile local positioning system can recalibrate after each movement. After the system has been calibrated, the inspection process can begin.

Figure 7B:
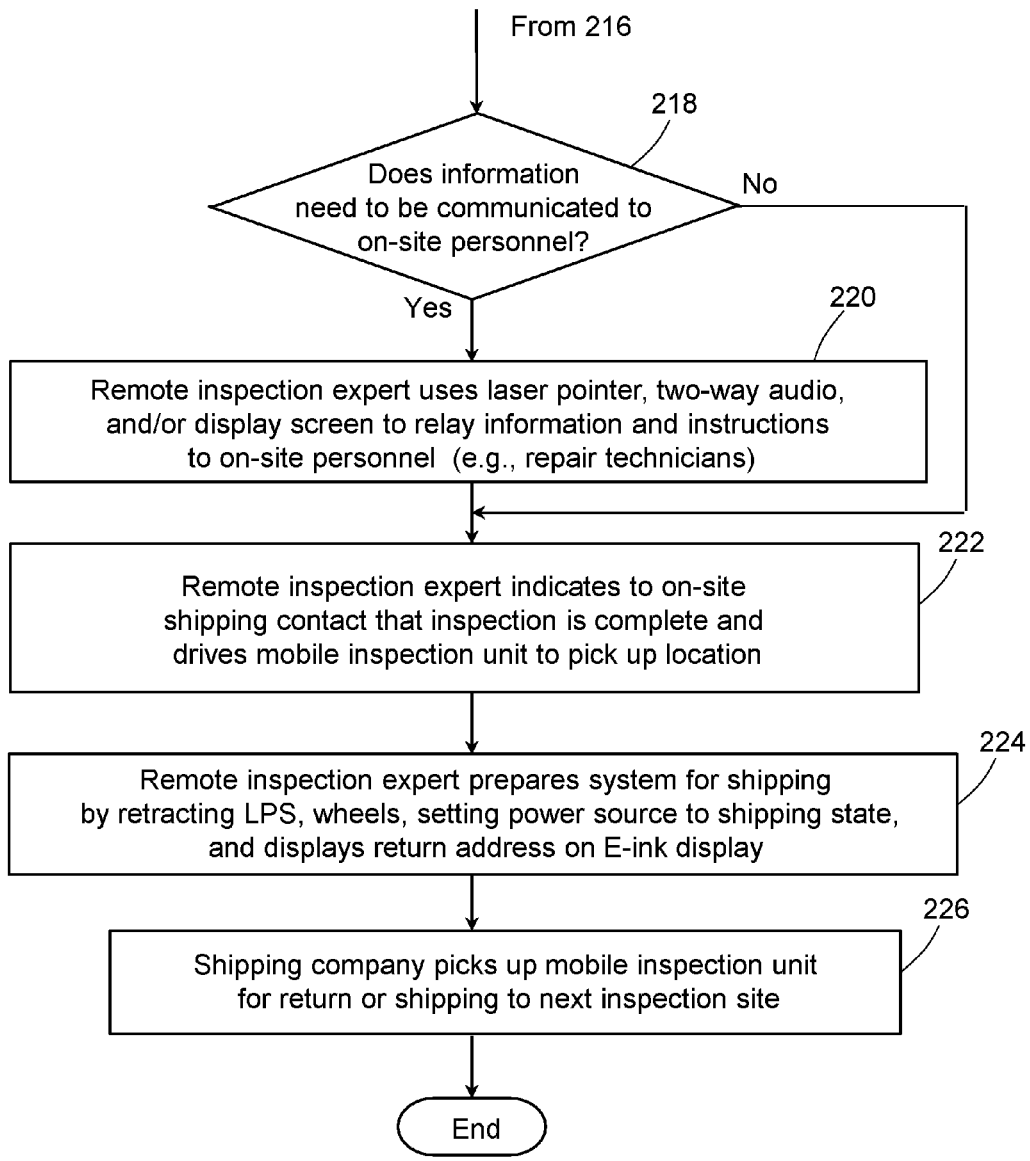
FIG. 7 is a diagram showing the mutual relationship of FIGS. 7A and 7B, which present respective portions of a flowchart showing a process for stand-off inspection of a target object at an inspection site utilizing the self-contained, remotely operable, mobile standoff measurement and inspection system depicted in FIG. 6.

FIGS. 7A and 7B present respective portions of a flowchart showing a process 200 for stand-off inspection of a target object at an inspection site utilizing the self-contained, remotely operable, mobile standoff measurement and inspection system depicted in FIG. 6. In this use case, an untrained on-site person receives the inspection equipment from a shipper (step 202 in FIG. 7A). That person places the inspection equipment on the ground in the general vicinity of the target object and then notifies the remote (i.e., off-site) inspection expert (by a phone call, email, or possibly by entering a code on the mobile inspection device itself) that the system has been delivered and is in place for the inspection (steps 204). The remote inspection expert establishes a communication connection with the on-board computer of the inspection system and then runs a system diagnostic check remotely (steps 206), which may include searching for an optimal data connection. When the automated system check has been completed and a data connection established, the remote inspection expert activates the deployment actuators (step 208). The remote inspection expert then commands the mobile measurement/inspection system to move to a location of interest near the target object and stop at the desired location (step 210). With the system at the desired location, the remote inspection expert calibrates the LPS to the local coordinate system of the target object (step 212) and then begins acquiring position measurements, capturing photographs or video, etc. (steps 214). After measurement and inspection have been completed for one location on the target object, the remote inspection expert determines whether data from other locations on the target object is required (step 216). If the decision is in the affirmative, then steps 210, 212, 214 and 216 are repeated for a new location on the target object. If the decision is in the negative, then the process proceeds to step 218 (see FIG. 7B).

Referring to FIG. 7B, upon completion of the inspection the remote inspection expert determines (step 218) whether information should be communicated to on-site personnel. If information should be communicated, the remote inspection expert may use a laser pointer, two-way audio and/or display screen on the mobile standoff measurement and inspection system to relay information and instructions to on-site personnel (e.g., repair technicians) (step 220). Thereafter the remote inspection expert indicates to the on-site shipping contact that the inspection has been completed and drives the mobile inspection unit to a pick-up location (steps 222). If a determination is made in step 218 that no information should be communicated, then steps 222 are performed without performing step 220. Then the remote inspection expert re-configures the mobile system for return shipment (steps 224), which may include retracting the LPS unit and wheels, setting the power source to a shipping state, and displaying the return shipping address on an E-ink display unit mounted to the exterior of the shipping container. The remote inspection expert then notifies the on-site personnel (or perhaps the shipping company directly) that the equipment is ready for pickup. The shipping company then picks up the mobile inspection unit for return or shipping to the next inspection site.

In cases where the structure to be inspected is located in an area having a rough (i.e., uneven) terrain, the self-contained mobile standoff measurement and inspection system can be designed to travel over the uneven terrain. One target application for this is for the inspection of pipelines where remote users need to acquire dimensional information for repairs.

Figure 8A:
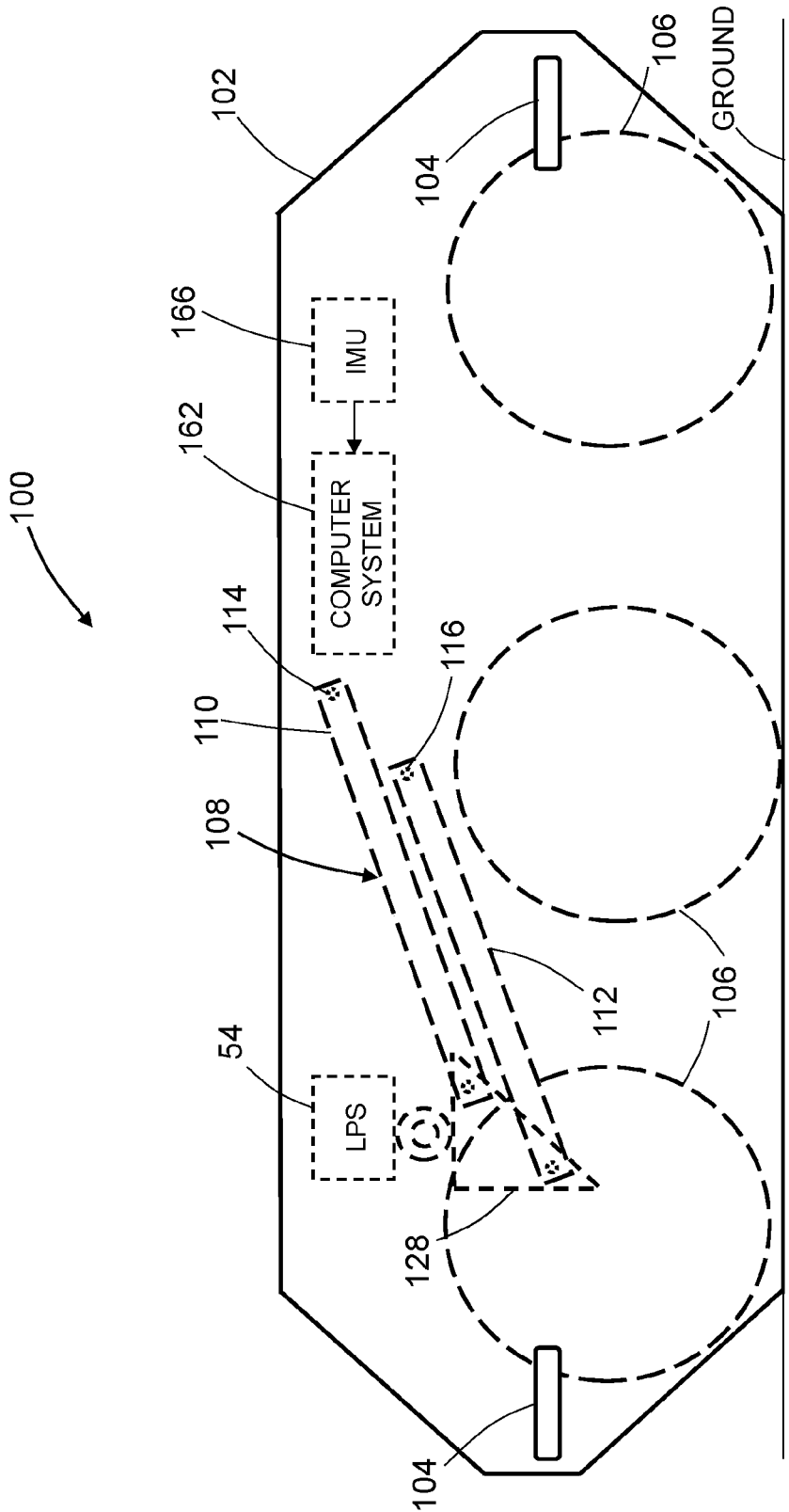
FIGS. 8A and 8B are diagrams representing side views of a rough-terrain mobile measurement and inspection system in accordance with another embodiment. The system is shown in a fully retracted configuration (FIG. 8A) suitable for shipping and a fully extended configuration (FIG. 8B) suitable for measurement and inspection of a structure. Hidden components (disposed inside the shipping container) are represented by dashed lines.
Figure 8B:
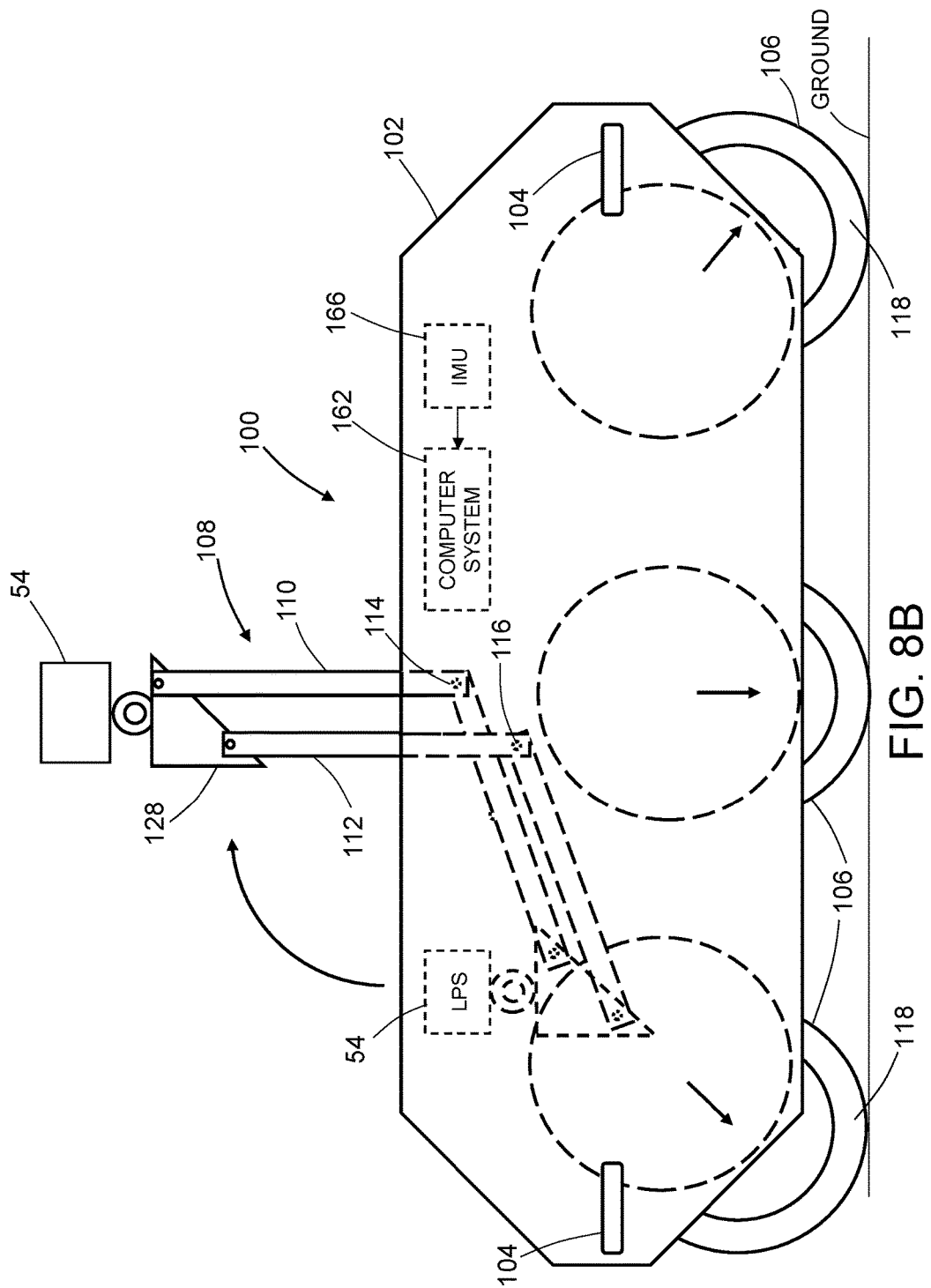

FIGS. 8A and 8B are diagrams representing side views of a self-contained rough-terrain mobile standoff measurement and inspection system (hereinafter "rough-terrain mobile measurement and inspection system 100) in accordance with one embodiment. The rough-terrain mobile measurement and inspection system 100 is shown in a fully retracted configuration suitable for shipping in FIG. 8A and in a fully extended configuration suitable for measurement and inspection in FIG. 8B.

The rough-terrain mobile measurement and inspection system 100 depicted at a high level in FIGS. 8A and 8B comprises a shipping container 102 equipped with four manually retractable handles 104, only two of which are visible in FIG. 8A. The other pair of handles 104 are attached to the opposite end of the shipping container 102. The handles 104 allow the rough-terrain mobile measurement and inspection system 100 to be manually lifted and carried. The shipping container 102 serves as a protective shell during shipment for the systems components, including deployable components intended to contact or interact with the environment at the inspection site. Hidden components disposed inside the shipping container 102 are represented by dashed lines. As seen in FIGS. 8A and 8B, a computer system 162 for controlling the operation of the system and an inertial measurement system (hereinafter "IMU 166") for tracking the non-level orientation of the system are disposed inside the shipping container 102. The IMU 166 is mounted inside the shipping container 102. Other components of the rough-terrain mobile measurement and inspection system 100 include the components identified in FIG. 6.

In the rough-terrain mobile measurement and inspection system 100 depicted in FIGS. 8A and 8B, the deployable components include a local positioning system 54 and a multiplicity of (e.g., six) compliant non-pneumatic tires 106. These are high-traction, off-road tires (such as knobby tires). While pneumatic tires are also possible, it is preferable to use compliant non-pneumatic or airless tires to eliminate the possibility of a flat tire when the shipping container arrives at its destination. Optionally, the system could also have compliant suspension between the wheels and supporting structure. The shipping container 102 may comprise motorized doors (not shown in FIGS. 8A and 8B) which open to allow extension of the deployable components and reclose after retraction of those same components. The deployable components fit inside the shipping container 102 when fully retracted and protrude outside the shipping container when fully extended. These subassemblies can be deployed in response to control signals output by the computer system 162, which in turn are output in response to commands from an NDI expert 36 at the operations command center. For example, the computer system 162 can be communicatively coupled to the operations command center by means of a transceiver disposed inside and an antenna disposed outside the shipping container 102. (Neither the transceiver nor the antenna are shown in FIG. 8A.)

In accordance with one proposed implementation, the rough-terrain mobile measurement and inspection system 100 has three pairs of compliant non-pneumatic tires 106. Only one compliant non-pneumatic tire 106 from each pair is visible in FIGS. 8A and 8B. Each compliant non-pneumatic tire 106 is linearly displaceable between a fully retracted position (seen in FIG. 8A) and a fully extended position (seen in FIG. 8B). More specifically, each compliant non-pneumatic tire 106 and the associated motor (not shown in FIGS. 8A and 8B) that drives its rotation are mounted to a support frame (also not shown) that is arranged to move linearly relative to a linear guide (not shown) disposed inside the shipping container 102. The mechanisms for enabling linear displacement of one component relative to a support structure are well known in the art. For example, motorized linear slides can be employed. As the compliant non-pneumatic tires 106 are extended, the lifting forces produced push the shipping container 102 off the ground. When the compliant non-pneumatic tires 106 are fully extended as seen in FIG. 8B, the rough-terrain mobile measurement and inspection system 100, but before the LPS unit 54 has been deployed, the rough-terrain mobile measurement and inspection system 100 will be in its travel configuration. In this configuration, the system can roll on whichever compliant non-pneumatic tires 106 are in contact with the uneven ground. One or more of the compliant non-pneumatic tires 78 may be a drive wheel that receives torque from a drivetrain and provides the driving force for moving the rough-terrain mobile measurement and inspection system 100 over the rough terrain.

As used herein, the term "compliant non-pneumatic tire" means an airless tire having a deformable outer circumferential surface that conforms to the shape of the ground surface that it contacts when the tire is pressed against the ground with sufficient force, e.g., the force due to the system weight. For example, each compliant non-pneumatic tire 106 may comprise a ring-shaped outer band 118 made of elastomeric material, an inner mounting band (not shown in FIGS. 8A and 8B), and a plurality of web spokes extending radially outward and connected at opposing ends to the inner and outer bands (not shown in FIGS. 8A and 8B). The inner mounting band anchors the tire to a hub. An additional layer of material in the form of treads may be bonded to the deformable outer circumferential surface of the outer band 118 to provide different traction and wear properties than the band material provides. The outer band 118 supports the load on the compliant non-pneumatic tire 106 and resiliently deforms to conform to the ground surface. The outer band 118 is preferably formed of an elastomeric material, such as natural and synthetic rubbers, polyurethanes, foamed rubbers and polyurethanes, segmented copolyesters, and block co-polymers of nylon. The web spokes may also be formed of an elastomeric material, which may be reinforced if desired.

Another deployable subassembly of the rough-terrain mobile measurement and inspection system 100 depicted in FIGS. 8A and 8B comprises an LPS unit 54 (including a video camera 2 mounted to a pan-tilt mechanism 3 and a laser range meter 25) and an extendible/retractable lift mechanism 108 (shown in an extended state in FIG. 8B) to which the LPS unit 54 is mounted. When lift mechanism 108 is retracted, the LPS unit 54 will be housed inside the shipping container 102, as shown in FIG. 8A. The lift mechanism 108 may comprise a first pair of pivotable arms 110 and a second pair of pivotable arms 112 of equal length. One end of each pivotable arm 110 is pivotably coupled to the body of shipping container 102 by a respective revolute joint 114, while one end of each pivotable arm 112 is pivotably coupled to the body of shipping container 102 by a respective revolute joint 116. The other ends of pivotable arms 110 and 112 are pivotably coupled to an LPS support block 128 to which the LPS unit 54 is affixed. In one implementation, rotation of the pivotable arms 110 and 112 is caused by a deployment actuator 60 (not shown in FIGS. 8A and 8B, but see FIG. 6). Various types of electromechanical actuators, capable of being powered by a battery, can be used. The deployment actuator 60 is controlled by the computer system 162 to cause the pivotable arms 110 and 112 to rotate in unison until the vertical position seen in FIG. 8B is reached. Stops may be provided for preventing rotation of the pivotable arms 110 and 112 to respective angular positions beyond a true vertical position. In this disclosure, references to "vertical" refer to a direction or an axis which would be perpendicular to the ground were the rough-terrain mobile measurement and inspection system 100 to be laid on flat ground in the manner depicted in FIG. 8A.

Following full extension of the LPS unit 54 (and the earlier full extension of the compliant non-pneumatic tires 106), the rough-terrain mobile measurement and inspection system 100 will be in its measurement configuration. After the system has been positioned at the commanded location, the NDI expert can send commands to the on-board computer system 162 instructing the LPS unit 54 to begin a calibration process.

The rough-terrain mobile measurement and inspection system 100 comprises on-board instrumentation capable of making dimensional measurements in the local coordinate system of the target object. More specifically, the on-board computer system 162 can be loaded with three-dimensional localization software of the type that uses multiple calibration points on the aircraft (item 30 in FIG. 5) to define the location (position and orientation) of video camera 2 relative to aircraft. This three-dimensional localization software was been described above.

Figure 9:
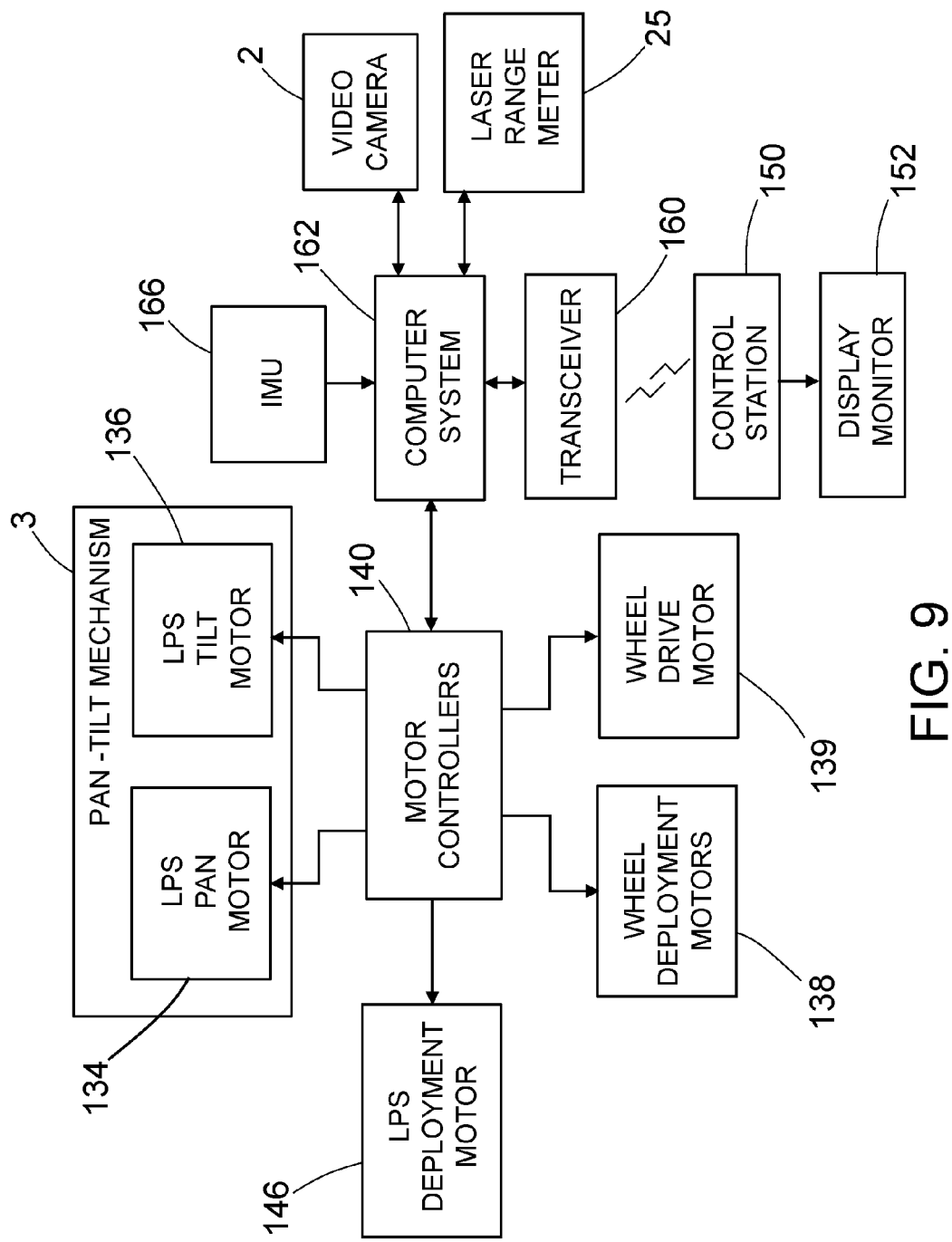
FIG. 9 is a block diagram identifying some components of the rough-terrain mobile measurement and inspection system depicted in FIGS. 8A and 8B.

FIG. 9 is a block diagram identifying some components of the rough-terrain mobile measurement and inspection system 100 depicted in FIGS. 8A and 8B. The LPS unit 54 (not indicated in FIG. 12) comprises a pan-tilt mechanism 3, a video camera 2 mounted to the pan-tilt mechanism 3, and a laser range meter 25 affixed to the video camera 2 in a manner such that the focal axis of the video camera 2 and the aim direction of the laser range meter 125 are mutually parallel. The pan-tilt mechanism 3 comprises an LPS pan motor 134 and an LPS tilt motor 136. The operation of the video camera 2 and the laser range meter 25 may be controlled by the on-board computer system 162.

The computer system 162 further communicates with a multiplicity of motor controllers 140, which respectively control the operation of LPS pan motor 134, LPS tilt motor 136, a multiplicity of wheel deployment motors 138, an LPS deployment motor 146 and at least one wheel drive motor 139. The LPS pan motor 134, when activated, drives rotation of the video camera 2 about a pan axis; the LPS tilt motor 136, when activated, drives rotation of the video camera 2 about a tilt axis. The pan-tilt mechanism 3 further comprises pan and tilt rotational encoders (not shown in the drawings) that send signals representing current angular position data back to the computer system 162. The LPS deployment motor 146, when activated, drives extension/retraction of the lift mechanism 108. The wheel deployment motors 138, when activated, drive extension/retraction of the compliant non-pneumatic tires 106. The at least one wheel drive motor 139, when activated, drives rotation of one of the compliant non-pneumatic tires 106. More than one of the compliant non-pneumatic tires 106 may be driven to rotate by a respective wheel drive motor 139.

The computer system 162 outputs control signals which are a function of radiofrequency commands transmitted by a control station 150. Those radiofrequency commands are received by a transceiver 160 on-board the rough-terrain mobile measurement and inspection system 100, converted into the proper digital format and then forwarded to the computer system 162. The control station 150 may comprise a general-purpose computer system configured with programming for controlling operation of the rough-terrain mobile measurement and inspection system 100 and its payload (e.g., LPS unit 54). For example, the pan and tilt angles of the pan-tilt mechanism 3, and therefore the orientation of the video camera 2, can be controlled using the keyboard, mouse, touchpad, or touchscreen of the computer system at the control station 150 or other user interface hardware (e.g., a gamepad). In addition, the computer system at the control station 150 is configured with programming for processing data received from the transceiver 160 during an inspection operation. In particular, the computer system of the control station 150 may comprise a display processor configured with software for controlling a display monitor 152 to display images acquired by the video camera 2. The optical image field, as sighted by the video camera 2, can be displayed on the display monitor 152.

The pan-tilt mechanism 3 is controlled to rotationally adjust the laser range meter 25 and the video camera 2 to selected angles around the pan and tilt axes. The aim direction vector, which describes the orientation of the laser range meter 25 (and the focal axis of the video camera 2) relative to the fixed coordinate system of the LPS unit 54, is determined from the pan and tilt angles when the laser range meter 25 is aimed at a point of interest on a target object.

The laser range meter 25 may be incorporated inside the housing of video camera 2 or mounted to the outside of video camera 2 in such a way that it transmits a laser beam along the aim direction vector. The laser range meter 25 is configured to measure the distance to any visible feature on or any marker attached to the target object. In accordance with some embodiments, the laser range meter 25 uses a laser beam to determine the distance to the target object. The most common form of laser range meter operates on the time-of-flight principle by sending a laser pulse in a narrow beam towards the target object and measuring the time taken by the pulse to be reflected off the target object and returned to a photodetector incorporated inside the laser range meter 25. With the speed of light known and an accurate measurement of the time made, the distance from the laser range meter 25 to the target object can be calculated. Many pulses are fired sequentially while the rough-terrain mobile measurement and inspection system 100 is stationary at a location and the average response is most commonly used.

Referring again to FIG. 9, the equipment on-board the system further comprises an IMU 166. An inertial measurement unit works by detecting linear acceleration using one or more accelerometers and rotational rate using one or more gyroscopes. In a typical configuration, an inertial measurement unit comprises one accelerometer and one gyroscope per axis for each of the three vehicle axes: pitch, roll and yaw. The computer system 162 may further comprise a separate processor configured with inertial navigation software that utilizes the raw IMU measurements to calculate angular rotation, angular rotation rates, linear velocity and position relative to a global reference frame. The data collected from the IMU 166 enables the computer system 162 to track the position of the rough-terrain mobile measurement and inspection system 100 using a method known as dead reckoning.

In cases where the structure to be inspected is located adjacent to a body of still liquid, the self-contained mobile standoff measurement and inspection system can be designed to float on the liquid. One use case is inspection of storage tanks to acquire dimensional information for repairs. Other use cases include cooling pools for reactors, shipyards, and perhaps swimming pools.

Figure 10:
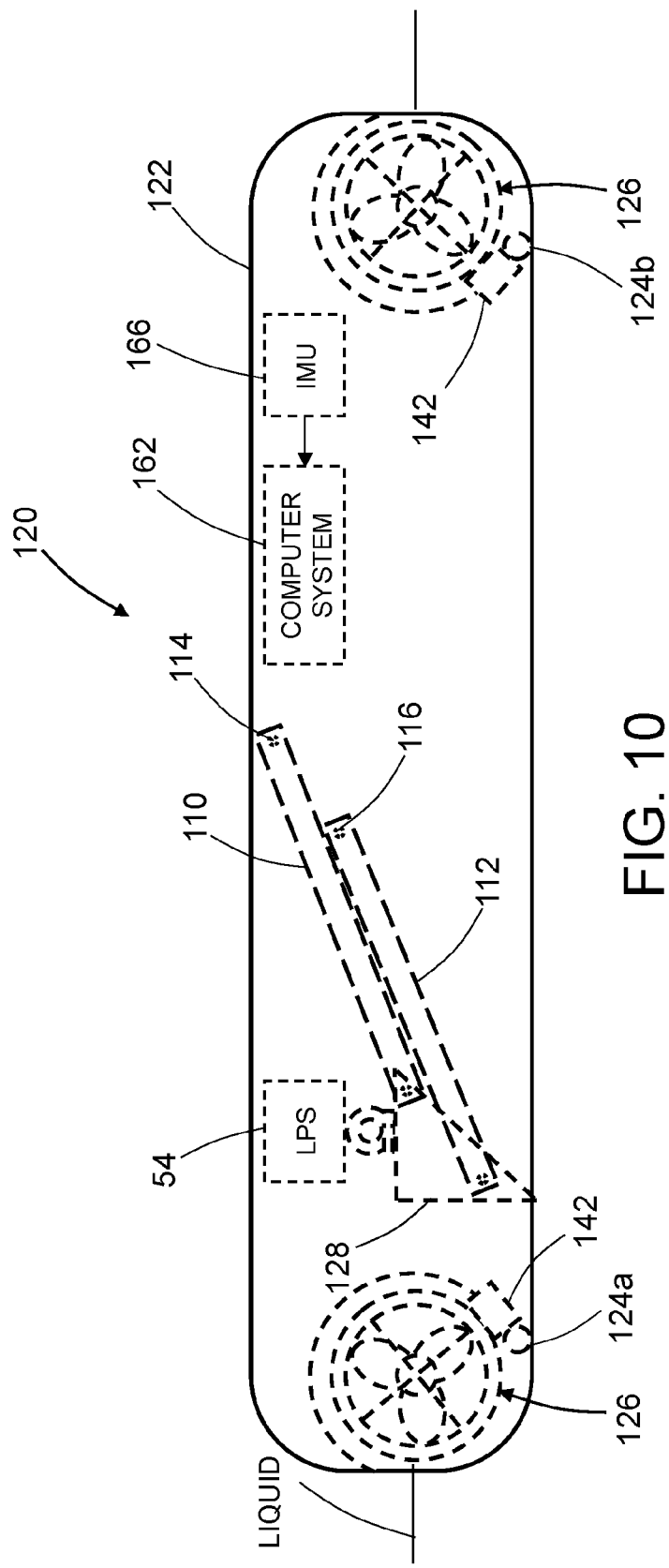
FIGS. 10 and 11A are diagrams representing side views of a floatable mobile measurement and inspection system in accordance with a further embodiment. The system is shown in a retracted configuration (FIG. 10) suitable for shipping and a fully extended configuration (FIG. 11A) suitable for measurement and inspection of a structure. Hidden components (disposed inside a shipping container) are represented by dashed lines.
Figure 11A:
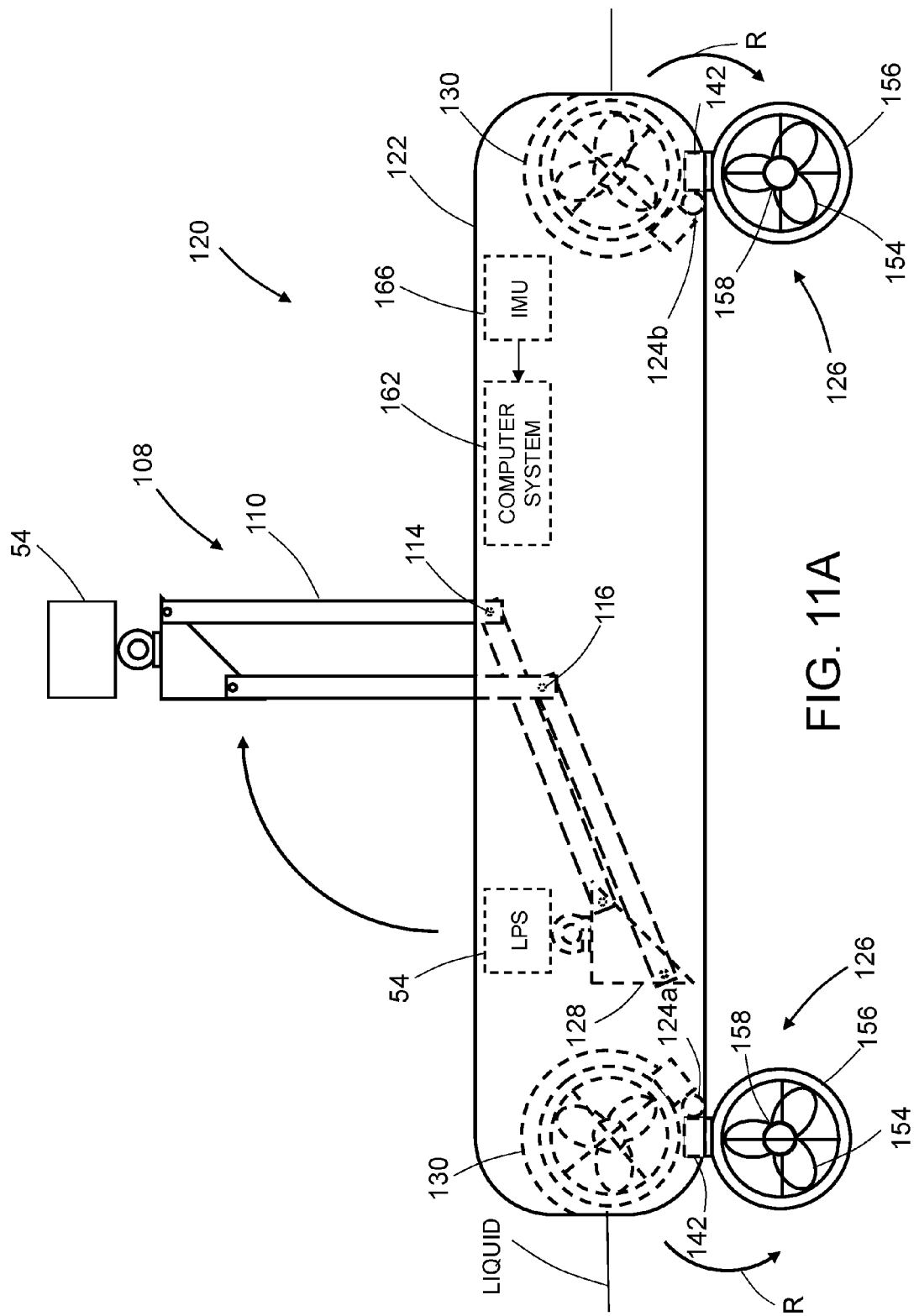

FIGS. 10 and 11A are diagrams representing side views of a self-contained floatable mobile standoff measurement and inspection system (hereinafter "floatable mobile measurement and inspection system 120") in accordance with one embodiment. The floatable mobile measurement and inspection system 120 is shown in a fully retracted configuration suitable for shipping in FIG. 10 and in a fully extended configuration suitable for measurement and inspection in FIG. 11A.

The floatable mobile measurement and inspection system 120 depicted at a high level in FIGS. 10 and 11A comprises a shipping container 122 equipped with four manually retractable handles 104 (not shown in FIGS. 10 and 11A to reduce clutter, but shown in FIG. 11B) as previously described. As seen in FIGS. 10 and 11A, a computer system 162 for controlling the operation of the system and an IMU 166 for tracking the location of the system are disposed inside the shipping container 122. The IMU 166 is mounted inside the shipping container 122. Other components of the floatable mobile measurement and inspection system 120 include the components identified in FIG. 6.

In the floatable mobile measurement and inspection system 120 depicted in FIGS. 10 and 11A, the deployable components include a local positioning system 54 and a multiplicity of (e.g., four) ducted propeller units 126. The shipping container 122 may comprise motorized doors as disclosed above. The computer system 162 can be communicatively coupled to an operations command center by means of a transceiver and an antenna as disclosed above.

In accordance with one proposed implementation, the floatable mobile measurement and inspection system 120 has two pairs of ducted propeller units 126. One pair of ducted propeller units 126 are fixedly mounted to opposing ends of a first horizontal shaft 124a; the other pair of ducted propeller units 126 are fixedly mounted to opposing ends of a second horizontal shaft 124b. The horizontal shafts 124a and 124b may be (but need not) be mutually parallel. Only one ducted propeller unit 126 from each pair is visible in FIGS. 10 and 11A. Each horizontal shaft rotates two ducted propeller units 126 into place from inside of the shipping container 122 to the outside. These rotations are indicated by curved arrows R in FIG. 11A. As seen in FIG. 11A, the horizontal shafts 124a and 124b are attached to the housings that contain the propeller yaw control motors 142. In this manner, each ducted propeller unit 126 is rotatable about a pitch axis between a fully retracted position inside a respective internal cavity 130 (seen in FIG. 10) and a fully extended position (seen in FIG. 11A).

Figure 11B:
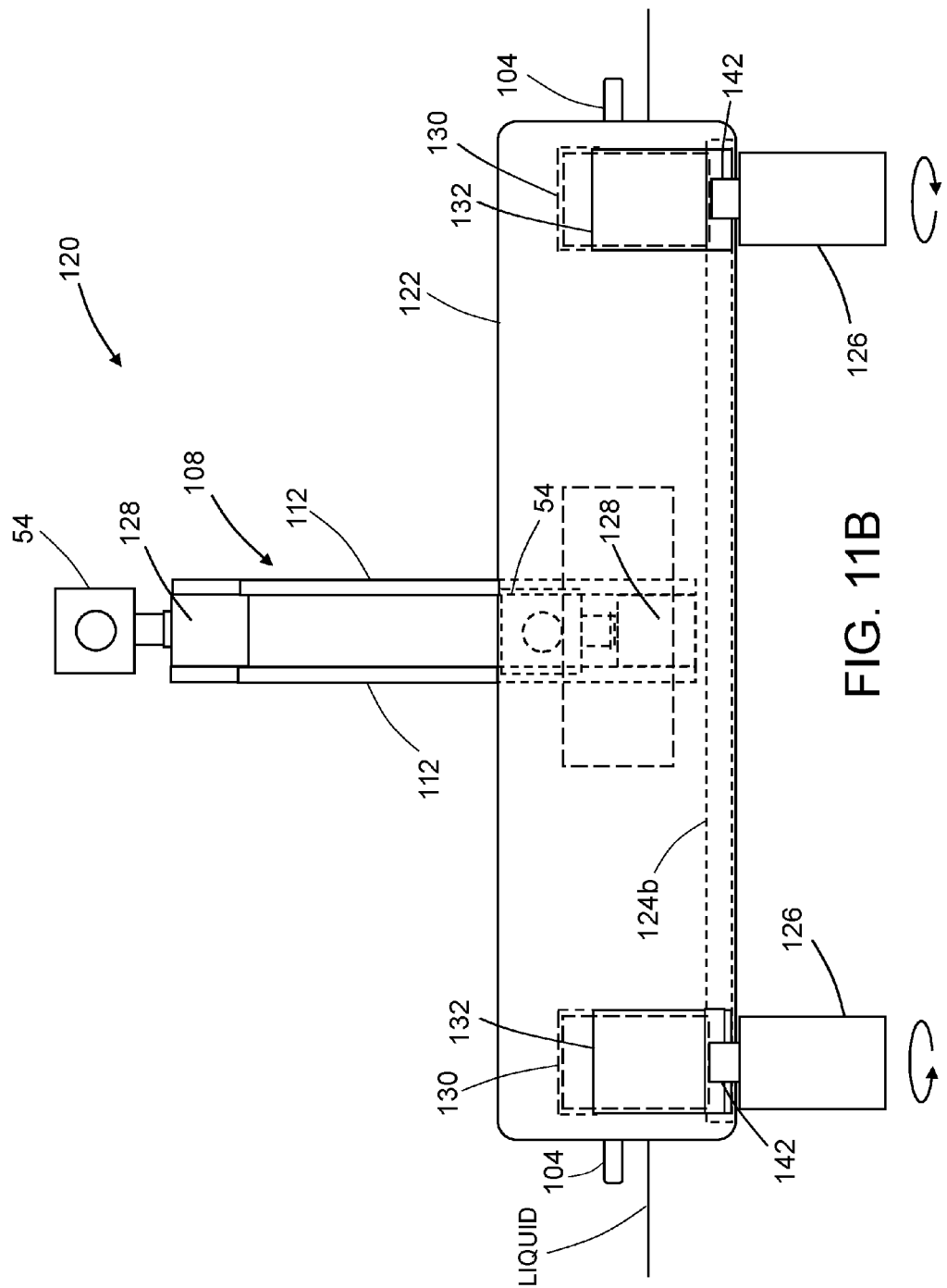
FIG. 11B is a diagram representing an end view of the floatable mobile measurement and inspection system when in its extended configuration as depicted in FIG. 11A.

FIG. 11B is a diagram representing an end view of the floatable mobile measurement and inspection system 120 when in its extended configuration. The internal cavities 130 are indicated by dashed lines in FIG. 11B. The openings 132 in shipping container 122—through which the ducted propeller units 126 pass when entering or leaving internal cavities 130—are indicated by solid lines in FIG. 11A.

When the ducted propeller units 126 are fully extended as seen in FIG. 11A, but before the LPS unit 54 has been deployed, the floatable mobile measurement and inspection system 120 will be in its travel configuration. Once each ducted propeller unit 126 has rotated out the shipping container 122 and locked into place, they can rotate independently about the yaw (i.e., vertical) axis for motion control (e.g., steering) as indicated by elliptical arrows in FIG. 11B. As seen in FIG. 11A, each ducted propeller unit 126 comprises a propeller 154, a nozzle 156 that surrounds the propeller 154, a propeller thrust motor 158 (supported by the nozzle 156) having an output shaft coupled to the propeller 154 for driving it to rotate to generate thrust, and a propeller yaw control motor 142 that drives rotation of the ducted propeller unit 126 about a yaw axis. The yaw angle, which is independently controllable for each ducted propeller unit 126, determines the direction of the thrust produced by each ducted propeller unit 126. Each ducted propeller unit 126 has independent thrust and yaw control. The steering of this platform works the same as a swerve drive for ground vehicles (except with ducted props instead of wheels, rotated 90 degrees).

The floatable mobile measurement and inspection system 120 depicted in FIGS. 10, 11A, and 11B further comprises an LPS unit 54 (including a video camera 2 mounted to a pan-tilt mechanism 3 and a laser range meter 25) and an extendible/retractable lift mechanism 108 (shown in an extended state in FIGS. 11A and 11B) that carries the LPS unit 54. The structure and function of the LPS unit 54 and the lift mechanism 108 of the floatable mobile measurement and inspection system 120 are the same as previously described for the same components of the rough-terrain mobile measurement and inspection system 100. When lift mechanism 108 is retracted, the LPS unit 54 will be housed inside the shipping container 122, as shown in FIG. 10.

Following full extension of the LPS unit 54 (and the earlier full extension of the ducted propeller units 126), the floatable mobile measurement and inspection system 120 will be in its measurement configuration. After the system has been positioned at the commanded location, the NDI expert can send commands to the on-board computer system 162 instructing the LPS unit 54 to begin a calibration process. The floatable mobile measurement and inspection system 120 comprises on-board instrumentation capable of making dimensional measurements in the local coordinate system of the target object. More specifically, the on-board computer system 162 can be loaded with the same three-dimensional localization software previously described.

Figure 12:
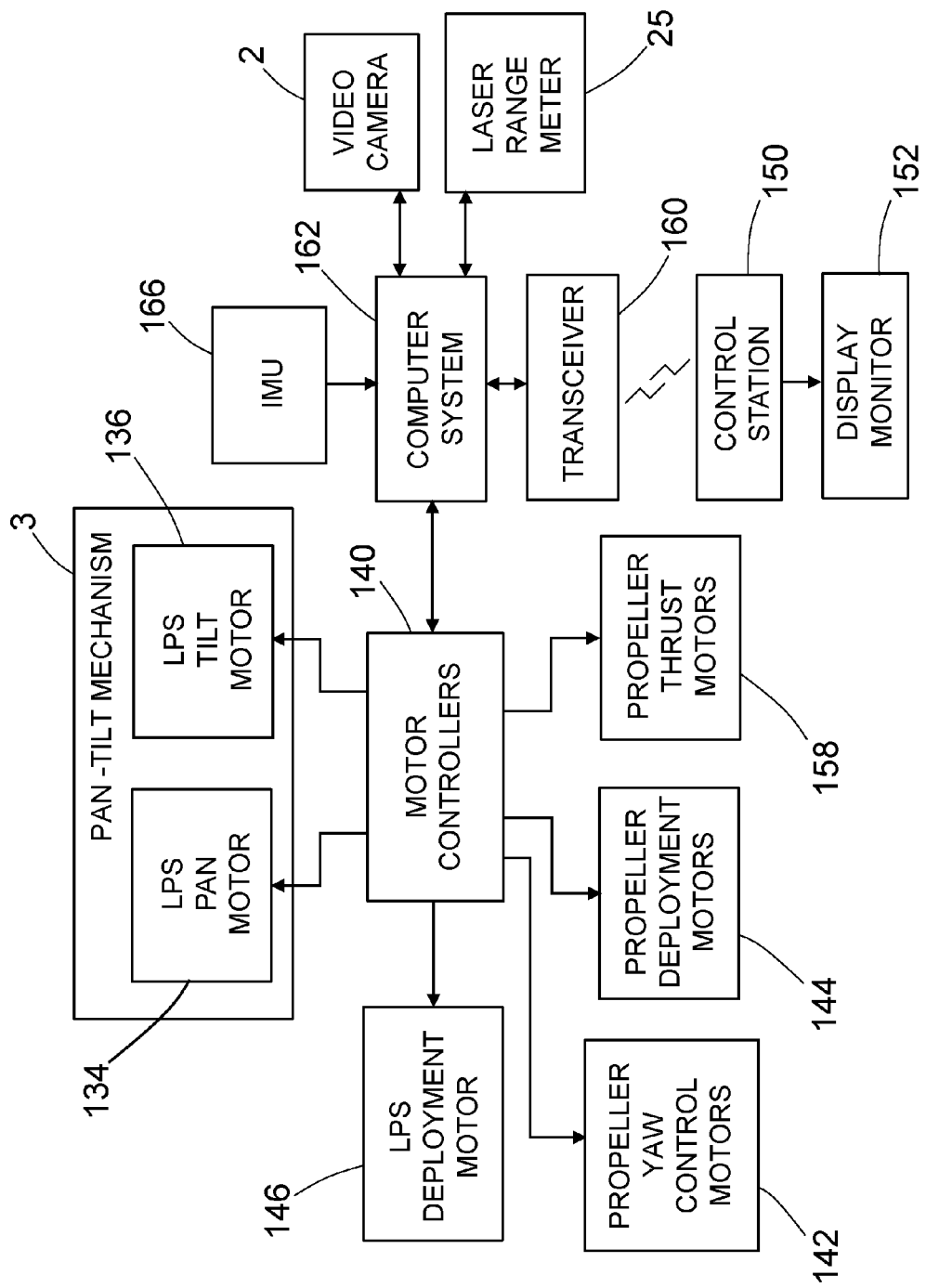
FIG. 12 is a block diagram identifying some components of the floatable mobile measurement and inspection system depicted in FIG. 10.

FIG. 12 is a block diagram identifying some components of the floatable mobile measurement and inspection system 120 depicted in FIG. 10. As previously described with reference to FIG. 9, the LPS unit (not indicated in FIG. 12) comprises a pan-tilt mechanism 3, a video camera 2 mounted to the pan-tilt mechanism 3, and a laser range meter 25 affixed to the video camera 2 in a manner such that the focal axis of the video camera 2 and the aim direction of the laser range meter 125 are mutually parallel. The pan-tilt mechanism 3 comprises an LPS pan motor 134 and an LPS tilt motor 136. The operation of the video camera 2 and the laser range meter 25 may be controlled by the on-board computer system 162.

The computer system 162 further communicates with a multiplicity of motor controllers 140, which respectively control the operation of LPS pan motor 134, LPS tilt motor 136, four propeller yaw control motors 142, four propeller deployment motors 144, an LPS deployment motor 146 and four propeller thrust motors 158. The LPS pan motor 134, when activated, drives rotation of the video camera 2 about a pan axis; the LPS tilt motor 136, when activated, drives rotation of the video camera 2 about a tilt axis. The LPS deployment motor 146, when activated, drives extension/retraction of the lift mechanism 108. The four propeller deployment motors 144, when activated, drive extension/retraction of the ducted propeller units 126. The four propeller thrust motors 158, when activated, cause the respective ducted propeller units 126 to generate thrust for propelling the floating system toward a destination.

The laser range meter 25 is configured to measure the distance to any visible feature on or any marker attached to the target object. In accordance with some embodiments, the laser range meter 25 uses a laser beam to determine the distance to the target object. The most common form of laser range meter operates on the time-of-flight principle by sending a laser pulse in a narrow beam towards the target object and measuring the time taken by the pulse to be reflected off the target object and returned to a photodetector incorporated inside the laser range meter 25. Many pulses are fired sequentially while the floatable mobile measurement and inspection system 120 floats at a location and the average response is most commonly used.

Referring again to FIG. 12, the equipment on-board the system further comprises an IMU 166. The computer system 162 may further comprise a separate processor configured with inertial navigation software that utilizes the raw IMU measurements to calculate angular rotation, angular rotation rates, linear velocity and position relative to a global reference frame. The data collected from the IMU 166 enables the computer system 162 to track the position of the floatable mobile measurement and inspection system 120 using a method known as dead reckoning.

Optionally, the rough-terrain mobile measurement and inspection system 100 or the floatable mobile measurement and inspection system 120 can each be equipped with an antenna and a GPS receiver, which receive geolocation and time information in a well-known manner. The GPS receiver may communicate with the computer system 162, which may include a processor configured to calculate the geolocation of the shipping container. The same processor can be further configured to check the system for correct right-side-up orientation for safe deployment (using orientation data acquired by IMU 166) and for correct position to make sure that the mobile system is at a correct site (using geolocation data acquired by the GPS receiver).

Using the system depicted in FIGS. 4 and 5, it is possible to determine the position and orientation of the motion base by using differential odometry—which uses encoders at the wheels and a planar kinematics algorithm to compute position and orientation. However, this methodology will need to be modified for rough-terrain mobile measurement and inspection system 100 as it travels on an uneven surface. The position and orientation estimates can be improved by using the orientation data from the IMU 166. This can be accomplished by converting the planar kinematics dead-reckoning algorithm into a three-dimensional spatial algorithm using three-axis orientation data from the IMU 166 to provide three-dimensional direction vector data to the dead reckoning algorithm. The location estimate can also be improved by GPS (since the vehicle will likely be outside).

It is a similar situation with the floating version. One cannot depend on using kinematics data from the propellers to give a reasonable estimate (since the platform does not stop immediately after the propellers stop moving), so one can use the IMU 166 and GPS data. But GPS data might not always be available for the use case inside of storage tanks, so one can use the acceleration data from the IMU 166 to give an estimate of position, at least for short durations. In these cases, using the LPS relative mode (described in U.S. Patent Application Publ. No. 2015/0268033 A1), with short amounts of time between measurements, will be a more reasonable approach than trying to get absolute measurements, since IMU position drift builds up over time.

The mobile telepresence systems disclosed above have the ability to perform point-to-point distance measurements, as well as acquire Cartesian coordinate data defined in the coordinate system of the target object. Combining a mobile platform with real-time tracking of platform position allows the position of the LPS unit to be precisely controlled by the remote operator or by a process executed by the on-board computer. The system is configured to allow for shipping to its destination without a separate shipping container. This allows the unit to be sent to the inspection site and automatically reconfigure to the mobile and inspection configurations without on-site assistance.

Additional features can be incorporated in the mobile measurement and inspection systems disclosed herein. Additional types of sensors can be deployed on the platform, such as temperature, humidity, and wind speed sensors to provide information concerning environmental conditions at the site to the remote operator. Proximity sensors can also be integrated into the mobile platform to help the system avoid collisions with objects in the environment as it moves. Wheels that enable holonomic motion of the vehicle can be used when additional maneuverability is required. For long inspection tasks, the remote operator may ask someone at the inspection site to plug in the unit to recharge, or to swap out a replaceable power source. In the event that flexible solar panels become available, the system may be equipped with a solar recharging option. Fuel cells or even motor-generator based power sources could be used. An integrated internal heater may be added for cold environments. Additional cameras (visible light or infrared) may be included for improved situational awareness. On-board lights can also be added to provide improved visibility in low-light conditions. Multiple types of networking options may be included: Wi-Fi, cell, etc. Additional sensors or actuators (e.g., grippers) could be included on the mobile platform. A liquid sensor can be used to detect when the floating system is launched into the liquid environment. (This would allow the system to add a check of the liquid status sensor to make sure that the system is actually floating on the liquid before deploying the ducted propeller units 126.) A gripper, magnetic, or suction attachment device can be used to stabilize a floating platform along a stationary object. Remotely extendable stabilizing jacks could be added to provide more secure footing for taking measurements for off-road variations of the system.

Optionally, any one of the measurement and inspection systems disclosed herein may be provided with an extendible/retractable marking device. The ability to mark the target object means that the on-site person need not be available to see the location(s) where the LPS points out damage to be repaired. An ink or paint sprayed onto the surface may be a valuable visual indication, even if a three-dimensional model and damage indication is provided to the inspector or repair personnel.

Since the concept is not limited to use in the aerospace industry, other types of manufacturing, architectural, and inspection businesses could also benefit from this technology. This capability would be particularly useful for use in areas that are not safe for humans. For example, in the event of a problem at a nuclear power plant, the ability to rapidly, safely and quantitatively measure the physical changes in the power plant structure and compare these changes to the CAD design data would be very useful.

While methods for controlling the operation of mobile measurement and inspection systems during non-destructive inspection of a structure have been described with reference to various embodiments, it will be understood by those skilled in the art that various changes may be made and equivalents may be substituted for elements thereof without departing from the scope of the teachings herein. In addition, many modifications may be made to adapt the teachings herein to a particular situation without departing from the scope thereof. Therefore it is intended that the claims not be limited to the particular embodiments disclosed herein.

As used herein, the term "location" comprises position in a three-dimensional coordinate system and orientation relative to that coordinate system.

As used herein, the term "computer system" should be construed broadly to encompass a system having at least one computer or processor, and which may have multiple computers or processors that communicate through a network or bus.

In addition, as used herein, the term "actuator" refers to an actuating subsystem that may comprise a motor or, in the alternative, may comprise a pneumatic or hydraulic actuator.

The methods described herein may be encoded as executable instructions embodied in a non-transitory tangible computer-readable storage medium, including, without limitation, a storage device and/or a memory device. Such instructions, when executed by a processor or computer, cause the processor or computer to perform at least a portion of the methods described herein.

The method claims set forth hereinafter should not be construed to require that the steps recited therein be performed in alphabetical order (any alphabetical ordering in the claims is used solely for the purpose of referencing previously recited steps) or in the order in which they are recited unless the claim language explicitly specifies or states conditions indicating a particular order in which some or all of those steps are performed. Nor should the method claims be construed to exclude any portions of two or more steps being performed concurrently or alternatingly unless the claim language explicitly states a condition that precludes such an interpretation.

APPENDIX

Figure 13:
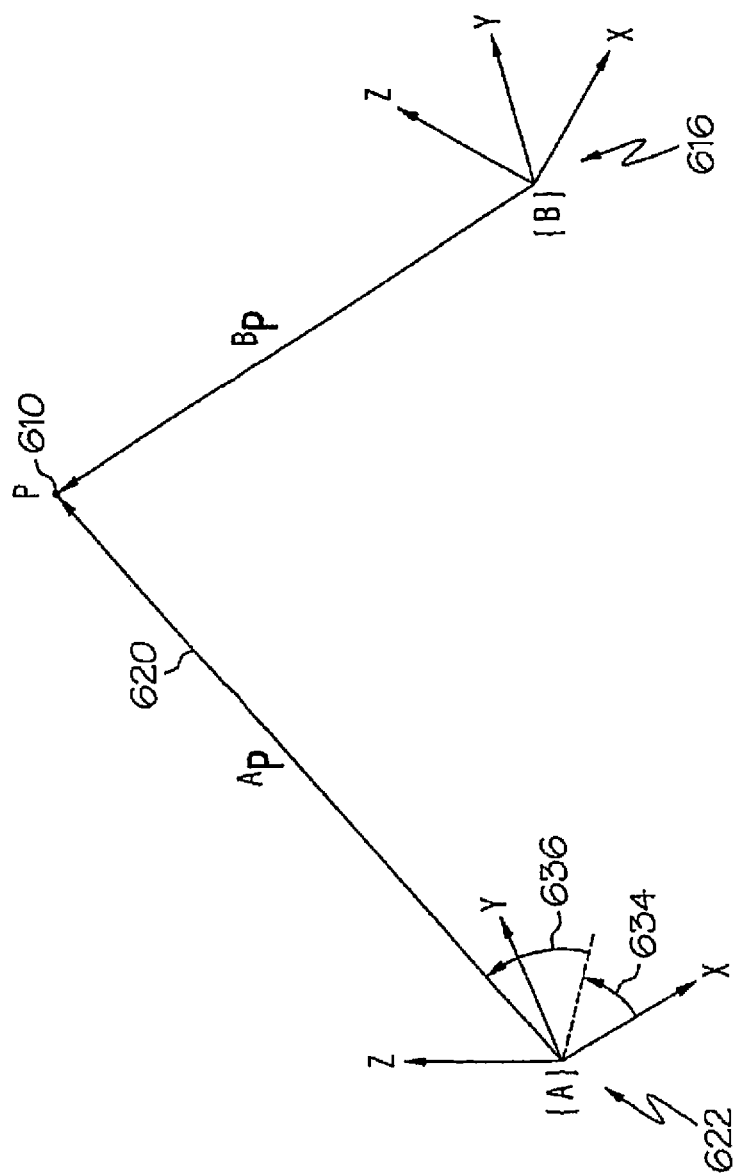
FIG. 13 is a diagram referred to in the Appendix and showing a position vector $^{A}P$ extending from the origin of an instrument coordinate system {A}, substantially along the aim point axis of the instrument, to a point of interest P and showing a position vector $^{B}P$ extending from the origin of a target object coordinate system {B} to the point of interest P.

FIG. 13 shows a position vector $^{A}P$ extending from the origin of an instrument coordinate system $\{A\}$, substantially along the aim point axis of the instrument, to a point of interest P and showing a position vector $^{B}P$ extending from the origin of a target object coordinate system $\{B\}$ to the point of interest P.

Referring to FIG. 13, when the coordinates of a point P in the instrument coordinate system 622 are spherical coordinates of pan (i.e., the pan angle 634 in FIG. 13 of a vector $^{A}P$ to the point P), tilt (the tilt angle 636 in FIG. 13 of the vector $^{A}P$ to the point P), and range (the distance along the vector $^{A}P$ to the point P in FIG. 13), the position of the point P represented as spherical coordinates in the instrument coordinate system 622 is related to the position of the point P in X,Y,Z Cartesian coordinates in the instrument coordinate system 622 from the following equations for the forward kinematics of the instrument 618:

$$X = \text{Range} * \cos(\text{pan}) * \cos(\text{tilt})$$

$$Y = \text{Range} * \sin(\text{pan}) * \cos(\text{tilt})$$

$$Z = \text{Range} * \sin(\text{tilt})$$

where pan (azimuth) is rotation about the Z axis and tilt (elevation) is rotation about the Y axis in the instrument coordinate system 622.

It is noted that the position of the point P represented as Cartesian coordinates (X,Y,Z) in the instrument coordinate system 622 is related to the position of the point P represented as spherical coordinates (pan, tilt, range) in the instrument coordinate system 622 from the following equations for the inverse kinematics of the instrument 618:

$$\text{pan} = \tan(Y, X)^{-1}$$

$$\text{tilt} = \tan(Z, \sqrt{X^2+Y^2})^{-1}$$

$$\text{Range} = \tan\sqrt{X^2+Y^2+Z^2}$$

In one implementation, a position $^BP$ (which is represented as a column vector in the form $[X,Y,Z,1]^T$) in the target object coordinate system 616 is calculated from a position $^AP$ (also a column vector in the form $[X,Y,Z,1]^T$) in the instrument coordinate system 622 from the equation:

$$^BP = {}_A^B T\, ^AP$$

where T is the calibration matrix. In one example, the calibration matrix is a 4×4 homogeneous transformation matrix having the form:

$${}_A^B T = \begin{bmatrix} r_{11} & r_{12} & r_{13} & X \\ r_{21} & r_{22} & r_{23} & Y \\ r_{31} & r_{32} & r_{33} & Z \\ 0 & 0 & 0 & 1 \end{bmatrix}$$

It is noted that a position $^AP$ in the instrument coordinate system 622 can be calculated from a position $^BP$ in the target object coordinate system 616 using the inverse of the calibration matrix from the equation:

$$^AP = ({}_A^B T)^{-1}\, ^BP = {}_B^A T\, ^BP$$

Figure 14:
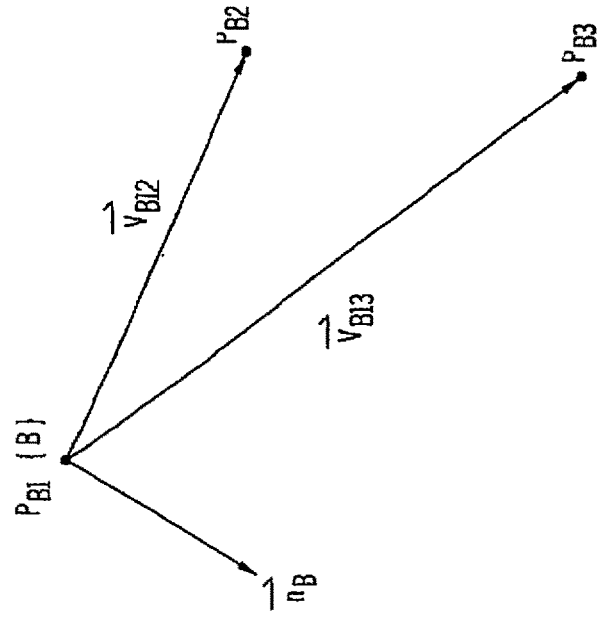
FIGS. 14-16 are diagrams referred to in the Appendix, where an illustrative method for calculating a calibration matrix for coordinate system transformation is described.
Figure 14:
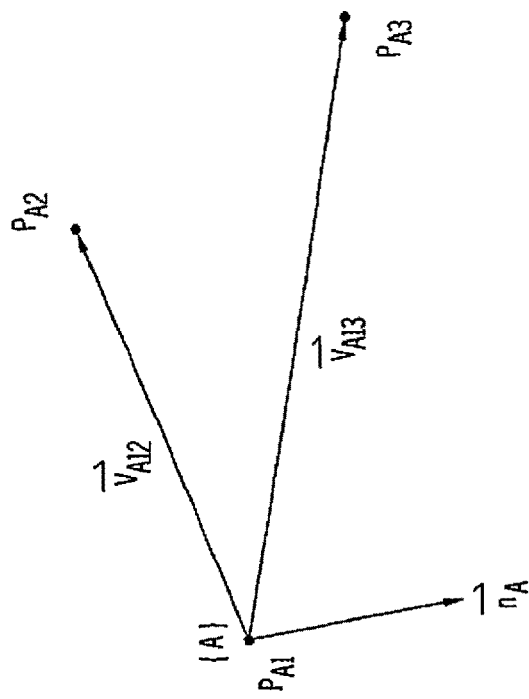
Figure 15:
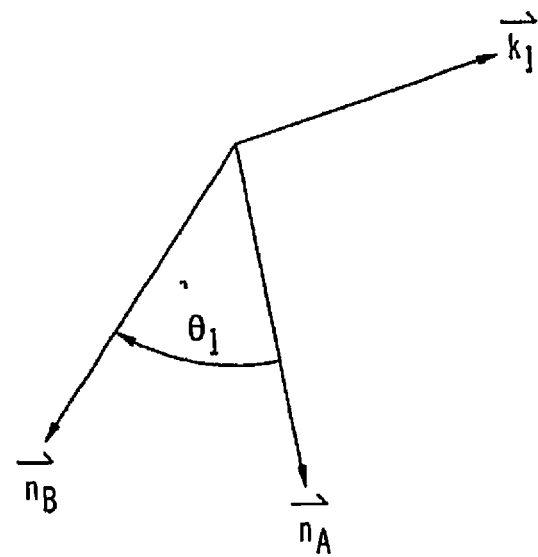
Figure 16:
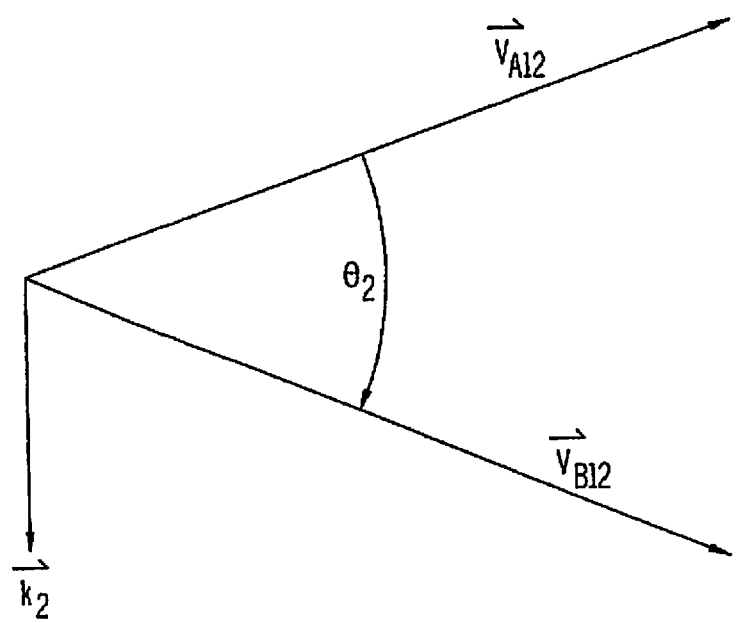

In one example, the three calibration points are non-collinear, and the calibration matrix is calculated as follows:

$$\vec{n}_A = \vec{V}_{A12} \times \vec{V}_{A13}$$

$$\vec{n}_B = \vec{V}_{B12} \times \vec{V}_{B13}$$

$$\vec{k}_1 = \vec{n}_A \times \vec{n}_B$$

$$\theta_1 = \alpha\cos(|\vec{n}_A| \cdot |\vec{n}_B|)$$

$$R_1 = f_1(|\vec{k}_1|, \theta_1)$$

$$\vec{k}_2 = \vec{V}_{A12} \times \vec{V}_{B12}$$

$$\theta_2 = \alpha\cos(|\vec{V}_{A12}| \cdot |\vec{V}_{B12}|)$$

$$R_2 = f_1(|\vec{k}_2|, \theta_2)$$

$$R_{12} = R_1 R_2$$

$${}_A^B T = [R_{12}, [R_1(\vec{V}_{B12} - \vec{V}_{A12})]^T]$$

$${}_B^A T = ({}_A^B T)^{-1}$$

wherein, referring to FIGS. 14-16:

$\vec{V}_{A12}$ is the vector in coordinate system A that extends from point $P_{A1}$ to $P_{A2}$;

$\vec{V}_{A13}$ is the vector in coordinate system A that extends from point $P_{A1}$ to $P_{A3}$;

$\vec{V}_{B12}$ is the vector in coordinate system A that extends from point $P_{B1}$ to $P_{B2}$;

$\vec{V}_{B13}$ is the vector in coordinate system A that extends from point $P_{B1}$ to $P_{B3}$;

$\vec{n}_A$ and $\vec{n}_B$ are the normals created from the vector cross products;

$\vec{k}_1$ and $\vec{k}_2$ are axes of rotation;

$\theta_1$ and $\theta_2$ are rotation angles about axes $\vec{k}_1$ and $\vec{k}_2$, respectively;

$R_1$, $R_2$, and $R_{12}$ are 3×3 symmetric rotation matrices; and $f_1(\ )$ is the function (known to those skilled in the art and described, for example, in "Introduction to Robotics: Mechanics and Control", 3rd edition, by John J. Craig and published July 2004 by Prentice Hall Professional Technical Reference) which generates a 3×3 rotation matrix from the angle-axis definition described below:

$$f_1(\hat{k}, \theta) = \begin{bmatrix} k_x k_x v\theta + c\theta & k_x k_y v\theta - k_z s\theta & k_x k_z v\theta + k_y s\theta \\ k_x k_y v\theta + k_z s\theta & k_y k_y v\theta + c\theta & k_y k_z v\theta - k_x s\theta \\ k_x k_z v\theta - k_y s\theta & k_y k_z v\theta + k_x s\theta & k_z k_z v\theta + c\theta \end{bmatrix}$$

where $c\theta = \cos(\theta)$, $s\theta = \sin(\theta)$, $v\theta = 1 - \cos(\theta)$, and $\hat{k} = [k_x, k_y, k_z]$.

Note that the 4×4 homogeneous calibration matrix ${}_A^B T$ only is computed once for any position of the pointing instrument relative to the target object, and ${}_A^B T$ can then be used to convert any number of vectors from coordinate system A (the instrument coordinate system 622) into coordinate system B (the target object coordinate system 616). It is also noted that the inverse calibration matrix ${}_B^A T$ can be calculated by calculating the inverse of the calibration matrix ${}_A^B T$ or can be calculated directly by switching the order of the vectors in the first equations of the previous paragraph.

The invention claimed is:

1. A mobile system comprising:
a shipping container;
a multiplicity of compliant non-pneumatic tires mechanically coupled to the shipping container for movement between respective retracted positions in a shipping configuration and respective extended positions in a deployed configuration;
a local positioning system unit mechanically coupled to the shipping container for movement between a retracted position inside the shipping container in the shipping configuration and an extended position outside the shipping container in the deployed configuration, the local positioning system unit comprising a laser range meter and a video camera;
a computer system disposed inside the shipping container;
a transceiver communicatively coupled to the computer system and capable of receiving commands from an in-range wireless network access point and transmitting the commands to the computer system;
a drivetrain disposed inside the shipping container for driving at least one of the compliant non-pneumatic tires to rotate;
a wheel deployment actuator disposed inside the shipping container for actuating movement of a first compliant non-pneumatic tire of the multiplicity of compliant non-pneumatic tires between its retracted and extended positions; and
a local positioning system unit deployment actuator disposed inside the shipping container for actuating movement of the local positioning system unit between its retracted and extended positions,
wherein the computer system is configured to perform the following operations:

controlling the wheel and local positioning system unit deployment actuators in response to deployment commands received via the transceiver;

controlling the drivetrain to move the shipping container to a location near a target object in accordance with a platform location command received via the transceiver when the compliant non-pneumatic tires are in their extended positions; and controlling the laser range meter to project wave energy toward a point on a surface of the target object.

2. The mobile system as recited in claim 1, wherein the computer system is further configured to control the local positioning system unit to calibrate its position and orientation relative to a coordinate system of the target object in response to a calibration command received via transceiver.

3. The mobile system as recited in claim 1, further comprising a lift mechanism pivotably coupled to the shipping container, coupled to the local positioning system unit deployment actuator, and having a stop position, wherein the local positioning system unit is mounted to the lift mechanism.

4. The mobile system as recited in claim 1, wherein the video camera has a focal axis, the laser range meter has an axis parallel to the focal axis of the video camera, and the video camera is mounted to a pan-tilt mechanism.

5. The mobile system as recited in claim 1, wherein each of the multiplicity of compliant non-pneumatic tires comprises a respective outer band made of elastomeric material.

6. The mobile system as recited in claim 1, further comprising an inertial measurement unit mounted inside the shipping container, wherein the computer system is configured to estimate a location of the mobile system based at least in part on signals received from the inertial measurement unit.

7. A method for teleoperation of a mobile system from a remote computer, comprising:
(a) configuring the mobile system comprising a shipping container so that a multiplicity of compliant non-pneumatic tires are in retracted positions and a local positioning system comprising a video camera and a laser range meter is in a retracted position in a shipping configuration;
(b) placing the mobile system in the shipping configuration on an uneven surface at a site;
(c) establishing a communication channel between a computer system inside the shipping container and the remote computer via a wireless connection while the mobile system is at the site; and
(d) via the wireless connection, remotely activating a transformation of the mobile system from the shipping configuration to a deployed configuration in which the compliant non-pneumatic tires and the local positioning system are in respective extended positions.

8. The method as recited in claim 7, further comprising checking the system for correct right-side-up orientation for safe deployment and correct position to make sure that the mobile system is at a correct site.

9. The method as recited in claim 7, further comprising:
remotely controlling rotation of at least one compliant non-pneumatic tire via the wireless connection to cause the mobile system in the deployed configuration to travel over the uneven surface to a location in proximity to a target object;
acquiring linear acceleration and rotational rate data using an inertial measurement system that is fixed relative to the shipping container as the mobile system travels over the uneven surface; and
using the linear acceleration and rotational rate data from the inertial measurement system and a dead reckoning algorithm to compute the position and orientation of the shipping container.

10. The method as recited in claim 9, further comprising:
activating remotely the laser range meter to measure a distance to a point on a surface of the target object; and
remotely activating the camera to capture an image of an area on the surface of the target object.

11. The method as recited in claim 7, further comprising transporting the mobile system in its shipping configuration from a remote site to the site after step (a) and before step (b).

12. A mobile system comprising:
a shipping container;
a multiplicity of ducted propeller units mechanically coupled to the shipping container for movement between respective retracted positions in a shipping configuration and respective extended positions in a deployed configuration;
a local positioning system unit mechanically coupled to the shipping container for movement between a retracted position inside the shipping container in the shipping configuration and an extended position outside the shipping container in the deployed configuration, the local positioning system unit comprising a laser range meter and a video camera;
a computer system disposed inside the shipping container;
a transceiver communicatively coupled to the computer system and capable of receiving commands from an in-range wireless network access point and transmitting the commands to the computer system;
a propeller deployment actuator disposed inside the shipping container for actuating movement of a first ducted propeller unit of the multiplicity of ducted propeller units between its retracted and extended positions; and
a local positioning system unit deployment actuator disposed inside the shipping container for actuating movement of the local positioning system unit between its retracted and extended positions,
wherein the computer system is configured to perform the following operations:
controlling the propeller and local positioning system unit deployment actuators in response to deployment commands received via the transceiver;
controlling the ducted propeller units to move the shipping container to a location near a target object in accordance with a platform location command received via the transceiver when the ducted propeller units are in their extended positions; and
controlling the laser range meter to project wave energy toward a point on a surface of the target object.

13. The mobile system as recited in claim 12, wherein the computer system is further configured to control the local positioning system unit to calibrate its position and orientation relative to a coordinate system of the target object in response to a calibration command received via the transceiver.

14. The mobile system as recited in claim 12, further comprising a lift mechanism pivotably coupled to the shipping container, coupled to the local positioning system unit deployment actuator, and having a stop position, wherein the local positioning system unit is mounted to the lift mechanism.

15. The mobile system as recited in claim 12, wherein the video camera has a focal axis, the laser range meter has an axis parallel to the focal axis of the video camera, and the video camera is mounted to a pan-tilt mechanism.

16. The mobile system as recited in claim 12, wherein each of the multiplicity of ducted propeller units comprises a propeller, a nozzle that surrounds the propeller, a propeller thrust motor supported by the nozzle and coupled to the propeller for driving it to rotate to generate thrust, and a propeller yaw control motor that drives rotation of the ducted propeller unit about a yaw axis, and wherein the computer system is further configured to control to propeller thrust motors and the propeller yaw control motors to provide independent thrust and yaw control for each ducted propeller unit.

17. The mobile system as recited in claim 12, further comprising an inertial measurement unit mounted inside the shipping container, wherein the computer system is configured to estimate a location of the mobile system based at least in part on signals received from the inertial measurement unit.

18. A method for teleoperation of a mobile system from a remote computer, comprising:
    (a) configuring the mobile system comprising a shipping container so that a multiplicity of ducted propeller units are in retracted positions and a local positioning system comprising a video camera and a laser range meter is in a retracted position in a shipping configuration;
    (b) establishing a communication channel between a computer system inside the shipping container and the remote computer via a wireless connection;
    (c) floating the mobile system in the shipping configuration on a surface of a body of liquid; and
    (d) via the wireless connection, remotely activating a transformation of the mobile system from the shipping configuration to a deployed configuration in which the ducted propeller units and the local positioning system are in respective extended positions.

19. The method as recited in claim 18, further comprising checking the system for correct right-side-up orientation for safe deployment and correct position to make sure that the mobile system is at a correct site.

20. The method as recited in claim 18, further comprising:
    remotely controlling rotation of each ducted propeller unit via the wireless connection to cause the mobile system in the deployed configuration to float to a location in proximity to a target object;
    acquiring linear acceleration and rotational rate data using an inertial measurement system that is fixed relative to the shipping container as the mobile system floats to the location; and
    using the linear acceleration and rotational rate data from the inertial measurement system and a dead reckoning algorithm to compute the position and orientation of the shipping container.

21. The method as recited in claim 20, further comprising:
    remotely activating the laser range meter to measure a distance to a point on a surface of the target object; and
    remotely activating the video camera to capture an image of an area on the surface of the target object.

22. The method as recited in claim 18, further comprising transporting the mobile system in its shipping configuration from a remote site to a site near the body of liquid after step (a) and before step (b).

* * * * *